United States Patent
Sutherland et al.

(10) Patent No.: US 9,394,348 B2
(45) Date of Patent: Jul. 19, 2016

(54) COLLAGEN-LIKE SILK GENES

(71) Applicant: Commonwealth Scientific and Industrial Research Organisation, Campbell, Australian Capital Territory (AU)

(72) Inventors: Tara D. Sutherland, Watson (AU); Victoria Shirley Haritos, Kingsville (AU); Sarah Weisman, Griffith (AU); John Alan Maurice Ramshaw, Pascoe Vale (AU); Yong Yi Peng, Bulleen (AU); Shoko Okada, Waramanga (AU); Andrew Allan Walker, Braddon (AU)

( * ) Notice: Subject to any disclaimer, the term of this patent is extended or adjusted under 35 U.S.C. 154(b) by 0 days.

(21) Appl. No.: 14/357,879

(22) PCT Filed: Nov. 15, 2012

(86) PCT No.: PCT/AU2012/001412
§ 371 (c)(1),
(2) Date: May 13, 2014

(87) PCT Pub. No.: WO2013/071356
PCT Pub. Date: May 23, 2013

(65) Prior Publication Data
US 2014/0288009 A1    Sep. 25, 2014

Related U.S. Application Data

(60) Provisional application No. 61/560,649, filed on Nov. 16, 2011.

(51) Int. Cl.
*A61K 47/42* (2006.01)
*C07K 14/435* (2006.01)

(52) U.S. Cl.
CPC ........... *C07K 14/43563* (2013.01); *A61K 47/42* (2013.01); *C07K 14/43568* (2013.01); *C07K 14/43577* (2013.01)

(58) Field of Classification Search
CPC ................................................ C07K 14/43563
See application file for complete search history.

(56) References Cited

U.S. PATENT DOCUMENTS

| | | | |
|---|---|---|---|
| 4,515,737 A | 5/1985 | Karino et al. |
| 4,943,674 A | 7/1990 | Houck et al. |
| 5,232,611 A | 8/1993 | Ohashi et al. |
| 5,643,672 A | 7/1997 | Marchi et al. |
| 5,856,451 A | 1/1999 | Olsen et al. |
| 5,939,288 A | 8/1999 | Thornburg |
| 5,981,718 A | 11/1999 | Olsen et al. |
| 6,013,250 A | 1/2000 | Cannell et al. |
| 6,129,770 A | 10/2000 | Deutz et al. |
| 6,139,851 A | 10/2000 | Omura et al. |
| 6,175,053 B1 | 1/2001 | Tsubouchi |
| 6,280,747 B1 | 8/2001 | Philippe et al. |
| 6,284,246 B1 | 9/2001 | Weisgerber et al. |
| 6,303,752 B1 | 10/2001 | Olsen et al. |
| 6,358,501 B1 | 3/2002 | Dietz et al. |
| 6,398,821 B1 | 6/2002 | Dias et al. |
| 6,416,558 B1 | 7/2002 | Ona et al. |
| 8,048,859 B2 | 11/2011 | Kumar et al. |
| 2004/0005363 A1 | 1/2004 | Tsukada et al. |
| 2004/0170590 A1 | 9/2004 | Fahnestock et al. |
| 2004/0170827 A1 | 9/2004 | Crighton |
| 2004/0199241 A1 | 10/2004 | Gravett et al. |
| 2005/0019297 A1 | 1/2005 | Philippe et al. |
| 2005/0054830 A1 | 3/2005 | Islam et al. |
| 2005/0055051 A1 | 3/2005 | Grafton |
| 2005/0089552 A1 | 4/2005 | Altman et al. |
| 2005/0130857 A1 | 6/2005 | Meesilpa et al. |
| 2005/0175825 A1 | 8/2005 | Hansen et al. |
| 2005/0266992 A1 | 12/2005 | Ohno et al. |
| 2005/0268443 A1 | 12/2005 | Ramkumar |
| 2006/0035336 A1 | 2/2006 | Hook et al. |
| 2007/0041952 A1 | 2/2007 | Guilak |
| 2009/0214614 A1 | 8/2009 | Everland |
| 2011/0238179 A1 | 9/2011 | Laurencin et al. |
| 2011/0293685 A1 | 12/2011 | Kuo et al. |
| 2012/0171257 A1 | 7/2012 | Inanç et al. |
| 2012/0172985 A1 | 7/2012 | Altman et al. |
| 2012/0189669 A1 | 7/2012 | Altschuler et al. |
| 2012/0195967 A1 | 8/2012 | Kaplan et al. |

FOREIGN PATENT DOCUMENTS

| | | |
|---|---|---|
| JP | 2000139755 | 5/2000 |
| JP | 2004284246 | 10/2004 |
| WO | WO 1993010154 | 5/1993 |
| WO | WO 2005045122 | 1/2004 |

(Continued)

OTHER PUBLICATIONS

Hagenau et al., Journal of Structural Biology, 175: 339-347, 2011.*
Kenchington, Silk Secretion in Sawflies, 1969, J Morph, 127: 355-362.*
Craig et al., Comparative architecture of silks, fibrous proteins and their encoding genes in insects and spiders, 2002, Comparative Biochemistry and Physiology, 133: 493-507.*
Antonicelli et al. (2007) "Elastin-Elastases and Inflamm-Aging" *Curr. Top. Dev. Biol.* 79:99-155.
Atkins (1967) "A Four-Strand Coiled-Coil Model for Some Insect Fibrous Proteins" *J Mol Biol* 24(1):139-141.

(Continued)

*Primary Examiner* — Amber D Steele
(74) *Attorney, Agent, or Firm* — Carol Francis; Bozicevic, Field & Francis LLP

(57) ABSTRACT

The present invention relates to silk proteins which can be used to produce silk with a collagen-like structure, as well as nucleic acids encoding such proteins. The present invention also relates to recombinant cells and/or organisms which synthesize silk proteins. Silk proteins of the invention can be used for a variety of purposes such as in the production of personal care products, plastics, textiles, and biomedical products.

28 Claims, 4 Drawing Sheets

(56) References Cited

FOREIGN PATENT DOCUMENTS

Figure 2:
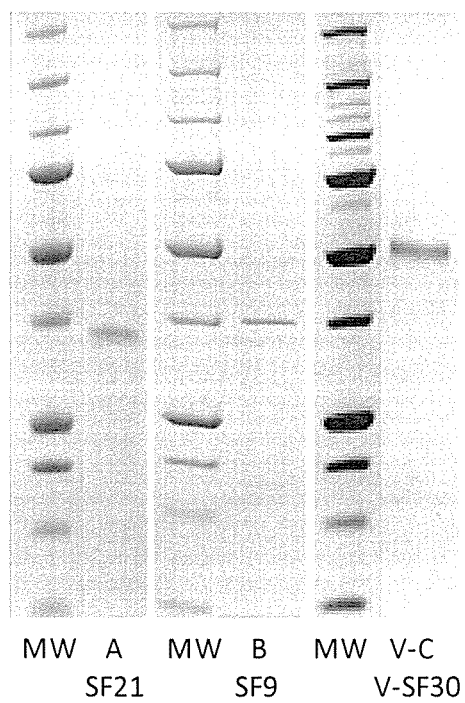

| WO | WO 2005017004 | 2/2005 |
|---|---|---|
| WO | WO 2007038837 | 4/2007 |
| WO | WO 2007057207 | 5/2007 |

OTHER PUBLICATIONS

Ayoub et al. (2007) "Blueprint for a High-Performance Biomaterial: Full-Length Spider Dragline Silk Genes" *J. Mol. Biol.* 24:139-141.

Bini et al. (2004) "Mapping Domain Structures in Silks From Insects and Spiders Related to Protein Assembly," *J Mol Biol.* 4 Jan. 2;335(1):27-40.

Craig & Riekel (2002) "Comparative Architecture of Silks, Fibrous Proteins and Their Encoding Genes in Insects and Spiders" *Comp Biochem Physiol B Biochem Mol Biol* 133(4):493-507.

Dal Pra et al. (2005) "De novo engineering of reticular connective tissue in vivo by silk fibroin nonwoven materials" *Biomaterials* 26:1987-1999.

Elvin et al. (2010) "A highly elastic tissue sealant based on photopolymerised gelatin" *Biomaterials* 31:8323-8331.

Gosline et al. (1999) "The Mechanical Design of Spider Silks: From Fibroin Sequence to Mechanical Function" *J. Exp. Biol.* 202:3295-303.

Hayashi and Lewis (2000) "Molecular Architecture and Evolution of a Modular Spider Silk Protein Gene" *Science* 287:1477-1479.

Hepburn et al. (1979) "Extensometric properties of insect fibroins: the green lacewing cross-β, honeybee α-helical and greater waxmoth parallel-β conformations." *Insect Biochemistry and Molecular Biology* 9:69-77.

Hepburn and Kurstjens (1988) "The Combs of Honeybees as Composite Materials" *Apidologie* 19:25-36.

International Preliminary Report on Patentability issued for PCT/AU2012/001412 on May 20, 2014.

Jin et al. (2002) "Electrospinning Bombyx mori Silk with Poly(ethylene oxide)" *Biomacromolecules* 3:1233-1239.

Kenchington (1969) "Silk secretion in sawflies," *Journal of Morphology*, vol. 127, No. 3, pp. 355-362.

Kim et al. (2005) "Three-dimensional aqueous-derived biomaterial scaffolds from silk fibroin" *Biomaterials* 26:2775-2785.

Lucas & Rudall (1968) "Extracellular Fibrous Proteins: The Silks" *Elsevier Publ.*, New York, NY, USA, pp. 475-558.

Nazarov et al. (2004) "Porous 3-D Scaffolds from Regenerated Silk Fibroin" *Biomacromolecules* 5:718-726.

Needleman & Wunsch (1970) "A General Method Applicable to the Search for Similarities in the Amino Acid Sequence of Two Proteins," *J Mol Biol.*, 48(3):443-453.

Persikov et al. (2005) "Prediction of Collagen Stability from Amino Acid Sequence" *J. Biol. Chem.* 280:19343-19349.

Ramshaw et al. (1998) "Gly-X-Y Tripeptide Frequencies in Collagen: A Context for Host—Guest Triple-Helical Peptides" *J. Struct. Bol.* 122:86-91.

Rost et al. (1993) "Prediction of protein secondary structure at better than 70% accuracy," *J Mol Biol.*, 20;232(2):584-599.

Rudall and Kenchington, (1971) "Arthropod Silks: The Problem of Fibrous Proteins in Animal Tissues," *Annual Review of Entomology*, vol. 16: 73-96.

Rudall (1962) "Silk and Other Cocoon Proteins" *In Comparative Biochemistry* (ed: Florkin and Mason) Academic Press, New York, 4:397-435.

Rudall (1968) "Comparative biology and biochemistry of collagen." In: *Treatise on Collagen* (ed BS Gould) London and New York: Academic, Chapter 2 2A:83-137.

Sehnal and Sutherland (2008) "Silks produced by insect labial glands," *Prion*, vol. 2, issue 4, pp. 145-153.

Spiro et al. (1971) "Glycosylation of Hydroxylysine in Collagens," *Nature New Biology*, vol. 231, No. 19, pp. 54-55.

Sutherland et al. (2006) "A Highly Divergent Gene Cluster in Honey Bees Encodes a Novel Silk Family" *Genome Res* 16(11):1414-1421.

Sutherland et al. (2010) "Insect Silk: One Name, Many Materials" *Annu. Rev. Entomol.* 55:171-88.

Tomita (2011) "Transgenic silkworms that weave recombinant proteins into silk cocoons" *Biotechnol. Lett.* 33:645-654.

Vepari and Kaplan (2007) "Silk as a Biomaterial" *Prog. Polym. Sci.* 32:991-1007.

Viney et al. (1993) "Processing and microstructurel control: lessons from natural materials" Materials Science Reports, 10(5):187-236.

Vollrath and Knight (2001) "Liquid crystalline spinning of spider silk" *Nature* 410: 541-548.

Zhang et al. (2012) "Stabilization of vaccines and antibiotics in silk and eliminating the cold chain" *PNAS* 109:11981-11986.

* cited by examiner

```
     1  ..74
b -         GRVGPAGEQGRQGPAGPPGPVGDRGQTGRSGQTGPQGPQGPSGPAGRQGKAGSVGETGKAGPAGPVGA
a - GPRGADGKIGPAGPQGPSGPAGPTGPVGPRGDAGRPGATGATGPDGPKGEFGPQGPSGPRGAPGPQGPAGPTGR
c - GPIGKEGPIGERGAAGPKGPVGQTGAVGDRGAVGAPGPNGRTGSVGVKGAQGQQGPSGPRGATGAAGPAGP
    .. . .*..*..* .*. **.*...*.**.**  *..* .*  .*. *..*   *  **..*...*..*  .*****..

75 ..148
b - TGPVGPAGAQGQTGAAGPRGAQGPQGPKGAMGPKGDQGPKGEQGQRGEQGAVGENGAPGPAGAKGATGAPGPKG
a - DGP        KGAAGPAGAAGPAGSPGAQGETGD   RGDRGLKGDVGAQGGKGIPGPAGPRGQTGPNGLPG
c -    AGPTGEQGATGAPGAAGPTGPPGLQGPRG   AKGVQGEKGPQGAQGNRGAPGVSGPRGPTGDRGQQG
    ........ .. **.*. **.** *...*..*. *. . .*..*..* .**.* .*.**..*..* ** * *

149 ..222
b - AQGDTGARGEDGVRGPAGPKGLNGQKGATGPVGPAGPKGRKGRV
a - AKGETGPKGAQGPAGPAGPKGEDGATGETGPRGPAGPAGAAGKD
c - AKGDVGAKGATGAPGAAGPRGPSGLKGATGNQGPAGPAGQAGED
    *.*..*..*. *. *.***.*  *  .*.**. *****.* .*...
```

Figure 1

SEQUENCE LISTING

<160> NUMBER OF SEQ ID NOS: 23

<210> SEQ ID NO 1
<211> LENGTH: 272
<212> TYPE: PRT
<213> ORGANISM: Nematus oligospilus

<400> SEQUENCE: 1

```
Met Arg Gln Val Ser Tyr Phe Ile Leu Ala Ala Val Ala Leu Phe Ala
1               5                   10                  15

Ile Phe Ala Glu Ala Val Pro Val Ala Thr Pro Ser Lys Gly Ser Lys
            20                  25                  30

Ser Gly His Gly Gly Glu Ser Gly Asn Tyr Gly His Gly Gly Arg Gly
        35                  40                  45

Gly Asp Gly Ser Asp Gly Gly Ala Gly Gly Val Gly Gly Gly Arg Ser
    50                  55                  60

Gly Gly Ser Gly Trp Ala Gly Pro Gln Gly Pro Arg Gly Ala Asp Gly
65                  70                  75                  80

Lys Ile Gly Pro Ala Gly Pro Gln Gly Pro Ser Gly Pro Ala Gly Pro
                85                  90                  95
```

```
Thr Gly Pro Val Gly Pro Arg Gly Asp Ala Gly Arg Pro Gly Ala Thr
                100                 105                 110

Gly Ala Thr Gly Pro Asp Gly Pro Lys Gly Glu Phe Gly Pro Gln Gly
            115                 120                 125

Pro Ser Gly Pro Arg Gly Ala Pro Gly Pro Gln Gly Pro Ala Gly Pro
        130                 135                 140

Thr Gly Arg Asp Gly Pro Lys Gly Ala Ala Gly Pro Ala Gly Ala Ala
145                 150                 155                 160

Gly Pro Ala Gly Ser Pro Gly Ala Gln Gly Glu Thr Gly Asp Arg Gly
                165                 170                 175

Asp Arg Gly Leu Lys Gly Asp Val Gly Ala Gln Gly Lys Gly Ile
            180                 185                 190

Pro Gly Pro Ala Gly Pro Arg Gly Gln Thr Gly Pro Asn Gly Leu Pro
        195                 200                 205

Gly Ala Lys Gly Glu Thr Gly Pro Lys Gly Ala Gln Gly Pro Ala Gly
        210                 215                 220

Pro Ala Gly Pro Lys Gly Glu Asp Gly Ala Thr Gly Glu Thr Gly Pro
225                 230                 235                 240

Arg Gly Pro Ala Gly Pro Ala Gly Ala Gly Lys Asp Ile Ile Ile
            245                 250                 255

Trp Lys Gly Gln Lys Gly Trp Arg Ser Pro Ser Glu Arg Lys Ser Tyr
            260                 265                 270

<210> SEQ ID NO 2
<211> LENGTH: 251
<212> TYPE: PRT
<213> ORGANISM: Nematus oligospilus

<400> SEQUENCE: 2

Val Pro Val Ala Thr Pro Ser Lys Gly Ser Lys Ser Gly His Gly Gly
1               5                   10                  15

Glu Ser Gly Asn Tyr Gly His Gly Gly Arg Gly Gly Asp Gly Ser Asp
            20                  25                  30

Gly Gly Ala Gly Gly Val Gly Gly Gly Arg Ser Gly Gly Ser Gly Trp
        35                  40                  45

Ala Gly Pro Gln Gly Pro Arg Gly Ala Asp Gly Lys Ile Gly Pro Ala
    50                  55                  60

Gly Pro Gln Gly Pro Ser Gly Pro Ala Gly Pro Thr Gly Pro Val Gly
65                  70                  75                  80

Pro Arg Gly Asp Ala Gly Arg Pro Gly Ala Thr Gly Ala Thr Gly Pro
                85                  90                  95

Asp Gly Pro Lys Gly Glu Phe Gly Pro Gln Gly Pro Ser Gly Pro Arg
            100                 105                 110

Gly Ala Pro Gly Pro Gln Gly Pro Ala Gly Pro Thr Gly Arg Asp Gly
        115                 120                 125

Pro Lys Gly Ala Ala Gly Pro Ala Gly Ala Ala Gly Pro Ala Gly Ser
    130                 135                 140

Pro Gly Ala Gln Gly Glu Thr Gly Asp Arg Gly Asp Arg Gly Leu Lys
145                 150                 155                 160

Gly Asp Val Gly Ala Gln Gly Lys Gly Ile Pro Gly Pro Ala Gly
                165                 170                 175

Pro Arg Gly Gln Thr Gly Pro Asn Gly Leu Pro Gly Ala Lys Gly Glu
            180                 185                 190

Thr Gly Pro Lys Gly Ala Gln Gly Pro Ala Gly Pro Ala Gly Pro Lys
        195                 200                 205
```

```
Gly Glu Asp Gly Ala Thr Gly Glu Thr Gly Pro Arg Gly Pro Ala Gly
        210                 215                 220
Pro Ala Gly Ala Ala Gly Lys Asp Ile Ile Trp Lys Gly Gln Lys
225                 230                 235                 240
Gly Trp Arg Ser Pro Ser Glu Arg Lys Ser Tyr
            245                 250

<210> SEQ ID NO 3
<211> LENGTH: 352
<212> TYPE: PRT
<213> ORGANISM: Nematus oligospilus

<400> SEQUENCE: 3

Met Arg Gln Ala Thr Phe Phe Ile Phe Ala Val Val Ala Val Phe Ala
1               5                   10                  15
Val Ala Gly Val Pro Val Pro Gly Asp Asp Gln Gly Arg Ala Glu Ser
                20                  25                  30
His Ala Ser Ala Ser Ser Ser Ala Gly Asn Gly Gly Asn Lys
            35                  40                  45
Gly Lys Ala Asp Ser Tyr Ala Glu Ala Asp Ser Tyr Ala Ser Ala Gly
50                  55                  60
Asn Asp Gly Lys Thr Gly Asn Ala Gly Ser Tyr Ala Ala Ala Gly Ser
65                  70                  75                  80
Ser Ala Ser Ala Gly Asn Asp Gly Asn Ala Gly Ser Tyr Ala Ser Gly
                85                  90                  95
Asn Ser Tyr Ala Asn Ala Gly Asn Asp Gly Asn Arg Gly Asn Arg Gly
            100                 105                 110
Asp Asp Gly Gly Arg Arg Gly Gln Gly Trp Gly Arg Val Gly Pro Ala
        115                 120                 125
Gly Glu Gln Gly Arg Gln Gly Pro Ala Gly Pro Pro Gly Pro Val Gly
    130                 135                 140
Asp Arg Gly Gln Thr Gly Arg Ser Gly Gln Thr Gly Pro Gln Gly Pro
145                 150                 155                 160
Gln Gly Pro Ser Gly Pro Ala Gly Arg Gln Gly Lys Ala Gly Ser Val
                165                 170                 175
Gly Glu Thr Gly Lys Ala Gly Pro Ala Gly Pro Val Gly Ala Thr Gly
            180                 185                 190
Pro Val Gly Pro Ala Gly Ala Gln Gly Gln Thr Gly Ala Ala Gly Pro
        195                 200                 205
Arg Gly Ala Gln Gly Pro Gln Gly Pro Lys Gly Ala Met Gly Pro Lys
    210                 215                 220
Gly Asp Gln Gly Pro Lys Gly Glu Gln Gly Gln Arg Gly Glu Gln Gly
225                 230                 235                 240
Ala Val Gly Glu Asn Gly Ala Pro Gly Pro Ala Gly Ala Lys Gly Ala
                245                 250                 255
Thr Gly Ala Pro Gly Pro Lys Gly Ala Gln Gly Asp Thr Gly Ala Arg
            260                 265                 270
Gly Glu Asp Gly Val Arg Gly Pro Ala Gly Pro Lys Gly Leu Asn Gly
        275                 280                 285
Gln Lys Gly Ala Thr Gly Pro Val Gly Pro Ala Gly Pro Lys Gly Arg
    290                 295                 300
Lys Gly Arg Val Ile Phe Met Asp Thr Pro Tyr Lys Gly Asp Asn Lys
305                 310                 315                 320
Gly Asp Asn Lys Gly Gly Asn Lys Tyr Asp Asn Lys Tyr Asp Asn Lys
```

```
                         325                 330                 335
Tyr Asp Asn Lys Tyr Asp Asn Lys Gly Asp Asn Lys Gly Gln Ser Tyr
            340                 345                 350

<210> SEQ ID NO 4
<211> LENGTH: 333
<212> TYPE: PRT
<213> ORGANISM: Nematus oligospilus

<400> SEQUENCE: 4

Val Pro Val Pro Gly Asp Asp Gln Gly Arg Ala Glu Ser His Ala Ser
1               5                   10                  15

Ala Ser Ser Ala Ser Ala Gly Asn Gly Gly Asn Lys Gly Lys Ala
            20                  25                  30

Asp Ser Tyr Ala Glu Ala Asp Ser Tyr Ala Ser Ala Gly Asn Asp Gly
            35                  40                  45

Lys Thr Gly Asn Ala Gly Ser Tyr Ala Ala Gly Ser Ser Ala Ser
50                  55                  60

Ala Gly Asn Asp Gly Asn Ala Gly Ser Tyr Ala Ser Gly Asn Ser Tyr
65                  70                  75                  80

Ala Asn Ala Gly Asn Asp Gly Asn Arg Gly Asn Arg Gly Asp Asp Gly
                85                  90                  95

Gly Arg Arg Gly Gln Gly Trp Gly Arg Val Gly Pro Ala Gly Glu Gln
            100                 105                 110

Gly Arg Gln Gly Pro Ala Gly Pro Pro Gly Pro Val Gly Asp Arg Gly
            115                 120                 125

Gln Thr Gly Arg Ser Gly Gln Thr Gly Pro Gln Gly Pro Gln Gly Pro
130                 135                 140

Ser Gly Pro Ala Gly Arg Gln Gly Lys Ala Gly Ser Val Gly Glu Thr
145                 150                 155                 160

Gly Lys Ala Gly Pro Ala Gly Pro Val Gly Ala Thr Gly Pro Val Gly
                165                 170                 175

Pro Ala Gly Ala Gln Gly Gln Thr Gly Ala Ala Gly Pro Arg Gly Ala
            180                 185                 190

Gln Gly Pro Gln Gly Pro Lys Gly Ala Met Gly Pro Lys Gly Asp Gln
            195                 200                 205

Gly Pro Lys Gly Glu Gln Gly Gln Arg Gly Glu Gln Gly Ala Val Gly
            210                 215                 220

Glu Asn Gly Ala Pro Gly Pro Ala Gly Ala Lys Gly Ala Thr Gly Ala
225                 230                 235                 240

Pro Gly Pro Lys Gly Ala Gln Gly Asp Thr Gly Ala Arg Gly Glu Asp
                245                 250                 255

Gly Val Arg Gly Pro Ala Gly Pro Lys Gly Leu Asn Gly Gln Lys Gly
            260                 265                 270

Ala Thr Gly Pro Val Gly Pro Ala Gly Pro Lys Gly Arg Lys Gly Arg
            275                 280                 285

Val Ile Phe Met Asp Thr Pro Tyr Lys Gly Asp Asn Lys Gly Asp Asn
            290                 295                 300

Lys Gly Asn Lys Tyr Asp Asn Lys Tyr Asp Asn Lys Tyr Asp Asn
305                 310                 315                 320

Lys Tyr Asp Asn Lys Gly Asp Asn Lys Gly Gln Ser Tyr
                325                 330

<210> SEQ ID NO 5
<211> LENGTH: 326
```

<212> TYPE: PRT
<213> ORGANISM: Nematus oligospilus

<400> SEQUENCE: 5

Met Arg Gln Val Ser Phe Leu Ile Phe Ala Ala Val Ala Leu Phe Val
1               5                   10                  15

Val Leu Gly Ala Asp Ala Arg Ser Val Lys Gly Lys Ser Gly Lys
            20                  25                  30

Gly Ser Gly Gly Lys Ser Gly Gly Tyr Asp Gly Arg Asn Asn Gly Gly
        35                  40                  45

Asn Asp Gly Gly Asn Asp Gly Asp Gly Ala Leu Ala Trp Met Gln
    50                  55                  60

Gly Pro Ile Gly Lys Glu Gly Pro Ile Gly Glu Arg Gly Ala Ala Gly
65                  70                  75                  80

Pro Lys Gly Pro Val Gly Gln Thr Gly Ala Val Gly Asp Arg Gly Ala
                85                  90                  95

Val Gly Ala Pro Gly Pro Asn Gly Arg Thr Gly Ser Val Gly Val Lys
            100                 105                 110

Gly Ala Gln Gly Gln Gln Gly Pro Ser Gly Pro Arg Gly Ala Thr Gly
        115                 120                 125

Ala Ala Gly Pro Ala Gly Pro Ala Gly Pro Thr Gly Glu Gln Gly Ala
    130                 135                 140

Thr Gly Ala Pro Gly Ala Ala Gly Pro Thr Gly Pro Pro Gly Leu Gln
145                 150                 155                 160

Gly Pro Arg Gly Ala Lys Gly Val Gln Gly Glu Lys Gly Pro Gln Gly
                165                 170                 175

Ala Gln Gly Asn Arg Gly Ala Pro Gly Val Ser Gly Pro Arg Gly Pro
            180                 185                 190

Thr Gly Asp Arg Gly Gln Gln Gly Ala Lys Gly Asp Val Gly Ala Lys
        195                 200                 205

Gly Ala Thr Gly Ala Pro Gly Ala Ala Gly Pro Arg Gly Pro Ser Gly
    210                 215                 220

Leu Lys Gly Ala Thr Gly Asn Gln Gly Pro Ala Gly Pro Ala Gly Gln
225                 230                 235                 240

Ala Gly Glu Asp Ala Val Tyr Pro Trp Asp Asn Lys Gly Ser Asp Asn
                245                 250                 255

Lys Gly Tyr Asp Asn Lys Gly Tyr Asp Asn Lys Gly Ser Asp Asn Lys
            260                 265                 270

Gly Tyr Asp Asn Lys Gly Tyr Asp Asn Lys Gly Tyr Asp Asn Lys Gly
        275                 280                 285

Tyr Asp Asn Lys Gly Tyr Asp Asn Lys Gly Tyr Asp Asn Lys Gly Tyr
    290                 295                 300

Asp Asn Lys Gly Tyr Val Asn Lys Asp Tyr Asp Asn Lys Gly Tyr Asp
305                 310                 315                 320

Asn Lys Gly Glu Ser Tyr
                325

<210> SEQ ID NO 6
<211> LENGTH: 304
<212> TYPE: PRT
<213> ORGANISM: Nematus oligospilus

<400> SEQUENCE: 6

Arg Ser Val Lys Gly Gly Lys Ser Gly Lys Gly Ser Gly Gly Lys Ser
1               5                   10                  15

Gly Gly Tyr Asp Gly Arg Asn Asn Gly Asn Asp Gly Gly Asn Asp
            20                  25                  30

Gly Gly Asp Gly Ala Leu Ala Trp Met Gln Pro Ile Gly Lys Glu
        35                  40                  45

Gly Pro Ile Gly Glu Arg Gly Ala Ala Gly Pro Lys Gly Pro Val Gly
    50                  55                  60

Gln Thr Gly Ala Val Gly Asp Arg Gly Ala Val Gly Ala Pro Gly Pro
65                  70                  75                  80

Asn Gly Arg Thr Gly Ser Val Gly Val Lys Gly Ala Gln Gly Gln Gln
                85                  90                  95

Gly Pro Ser Gly Pro Arg Gly Ala Thr Gly Ala Ala Gly Pro Ala Gly
            100                 105                 110

Pro Ala Gly Pro Thr Gly Glu Gln Gly Ala Thr Gly Ala Pro Gly Ala
        115                 120                 125

Ala Gly Pro Thr Gly Pro Pro Gly Leu Gln Gly Pro Arg Gly Ala Lys
    130                 135                 140

Gly Val Gln Gly Glu Lys Gly Pro Gln Gly Ala Gln Gly Asn Arg Gly
145                 150                 155                 160

Ala Pro Gly Val Ser Gly Pro Arg Gly Pro Thr Gly Asp Arg Gly Gln
                165                 170                 175

Gln Gly Ala Lys Gly Asp Val Gly Ala Lys Gly Ala Thr Gly Ala Pro
            180                 185                 190

Gly Ala Ala Gly Pro Arg Gly Pro Ser Gly Leu Lys Gly Ala Thr Gly
        195                 200                 205

Asn Gln Gly Pro Ala Gly Pro Ala Gly Gln Ala Gly Glu Asp Ala Val
210                 215                 220

Tyr Pro Trp Asp Asn Lys Gly Ser Asp Asn Lys Gly Tyr Asp Asn Lys
225                 230                 235                 240

Gly Tyr Asp Asn Lys Gly Ser Asp Asn Lys Gly Tyr Asp Asn Lys Gly
                245                 250                 255

Tyr Asp Asn Lys Gly Tyr Asp Asn Lys Gly Tyr Asp Asn Lys Gly Tyr
            260                 265                 270

Asp Asn Lys Gly Tyr Asp Asn Lys Gly Tyr Asp Asn Lys Gly Tyr Val
        275                 280                 285

Asn Lys Asp Tyr Asp Asn Lys Gly Tyr Asp Asn Lys Gly Glu Ser Tyr
    290                 295                 300

<210> SEQ ID NO 7
<211> LENGTH: 819
<212> TYPE: DNA
<213> ORGANISM: Nematus oligospilus

<400> SEQUENCE: 7
atgagacaag tcagctactt catcctcgcc gcggtggcac tattcgccat cttcgccgag      60
gcagttccag tagcaactcc atcgaagggc agcaagagcg tcacggtgg cgaatccggc     120 aactacggtc acggcggtcg cggtggtgac ggcagcgacg tggtgccgg tgtgtcggc     180 ggcggccgca gcggcggcag cggctgggca ggccccagg accacgagg tgccgatggt     240 aaaatcggac cagcaggtcc ccagggtccc agtggtcctg ccggacccac aggtccagtc     300
ggcccccgag agacgccgg aagaccgggc gccaccggtg ccaccggtcc agacggtccc     360
aaaggcgaat tggtcccca aggcccatcc ggtcccagag cgcaccagg tccccaaggt     420 ccagccgggc caaccggtcg tgacggtccg aaggtgcag ctggtccagc tggcgcagcc     480
ggtcccgcag gttcacccgg tgcccagggt gagaccggcg accgtggtga ccgaggactg     540

```
aagggagacg tcggtgccca aggtggcaag ggaatcccag gcccagcagg ccccagagga    600
cagaccggac ccaacggact ccctggagca aagggagaaa ccggccccaa gggagctcaa    660
ggacccgccg gcccagcagg gcccaaggga gaagatggag ccacgggaga gaccggcccc    720
aggggaccag ctggcccagc tggcgcagcg ggtaaagaca tcatcatctg gaagggacag    780
aagggatgga gatcaccaag cgaaagaaaa agctactag                           819

<210> SEQ ID NO 8
<211> LENGTH: 756
<212> TYPE: DNA
<213> ORGANISM: Nematus oligospilus

<400> SEQUENCE: 8
gttccagtag caactccatc gaagggcagc aagagcggtc acggtggcga atccggcaac     60
tacggtcacg gcggtcgcgg tggtgacggc agcgacggtg gtgccggtgg tgtcggcggc    120
ggccgcagcg gcggcagcgg ctgggcaggc ccccagggac cacgaggtgc cgatggtaaa    180
atcggaccag caggtcccca gggtcccagt ggtcctgccg gacccacagg tccagtcggc    240
ccccgaggag acgccggaag accgggcgcc accggtgcca ccggtccaga cggtcccaaa    300
ggcgaatttg gtccccaagg cccatccggt cccagaggcg caccaggtcc ccaaggtcca    360
gccgggccaa ccggtcgtga cggtccgaag ggtgcagctg gtccagctgg cgcagccggt    420
cccgcaggtt cacccggtgc ccagggtgag accggcgacc gtggtgaccg aggactgaag    480
ggagacgtcg gtgcccaagg tggcaaggga atcccaggcc cagcaggccc cagaggacag    540
accggaccca acggactccc tggagcaaag ggagaaaccg gccccaaggg agctcaagga    600
cccgccggcc cagcagggcc caagggagaa gatggagcca cgggagagac cggccccagg    660
ggaccagctg gcccagctgg cgcagcgggt aaagacatca tcatctggaa gggacagaag    720
ggatggagat caccaagcga aagaaaaagc tactag                              756

<210> SEQ ID NO 9
<211> LENGTH: 1059
<212> TYPE: DNA
<213> ORGANISM: Nematus oligospilus

<400> SEQUENCE: 9
atgagacaag ccaccttctt catcttcgcc gttgtggcag tattcgctgt cgctggtgtt     60
ccagtcccgg gagacgacca aggcagagcc gaaagccacg ctagcgccag cagctccgcc    120
agcgccggca acggcggcaa caaaggcaaa gccgacagct acgccgaagc cgacagctac    180
gccagcgccg gaaacgacgg taaaaccggc aacgccggaa gctatgccgc agccggaagc    240
tccgccagcg ccggcaacga cggcaatgcc ggaagctacg ccagcggcaa cagctacgcc    300
aacgccggca acgacggaaa ccgcggcaac cgcggagacg acggcggtcg tcgcggtcag    360
ggatggggta gagtaggacc agccggcgaa caaggccgac aaggaccagc cggtccaccc    420
ggtccagtag gagacagagg acagaccggc cgatcgggtc aaaccggtcc acaaggccca    480
cagggtccct caggcccagc aggacgccaa ggtaaggccg gttccgtcgg tgagaccggc    540
aaggctggtc cagctggccc agtaggtgca accggcccgg taggtccagc cggtgcccaa    600
ggccaaaccg gagccgccgg cccacgagga gcgcagggac cacagggccc caagggtgcg    660
atgggaccca agggcgacca aggacccaaa ggagagcaag gccagagagg tgaacaaggt    720
gccgtgggcg agaacggcgc acctggccca gccggagcca agggagcgac tggcgcacca    780
```

| | |
|---|---|
| ggtcccaagg gagcccaggg cgataccgga gcacgaggtg aagatggagt ccgtggacca | 840 |
| gctggcccca agggtttgaa cggccagaag ggagcgaccg gaccagtagg tccagccggc | 900 |
| ccaaagggac gcaagggtcg agtgatcttc atggacaccc atacaaggg agacaacaag | 960 |
| ggagacaaca agggcggcaa caagtacgac aacaagtacg acaacaagta cgacaacaag | 1020 |
| tacgacaaca agggcgacaa caagggacaa tcgtactaa | 1059 |

<210> SEQ ID NO 10
<211> LENGTH: 1002
<212> TYPE: DNA
<213> ORGANISM: Nematus oligospilus

<400> SEQUENCE: 10

| | |
|---|---|
| gttccagtcc cgggagacga ccaaggcaga gccgaaagcc acgctagcgc cagcagctcc | 60 |
| gccagcgccg gcaacggcgg caacaaaggc aaagccgaca gctacgccga agccgacagc | 120 |
| tacgccagcg ccggaaacga cggtaaaacc ggcaacgccg gaagctatgc cgcagccgga | 180 |
| agctccgcca gcgccggcaa cgacggcaat gccggaagct acgccagcgg caacagctac | 240 |
| gccaacgccg gcaacgacgg aaaccgcggc aaccgcggag acgacggcgg tcgtcgcggt | 300 |
| cagggatggg gtagagtagg accagccggc gaacaaggcc gacaaggacc agccggtcca | 360 |
| cccggtccag taggagacag aggacagacc ggccgatcgg gtcaaaccgg tccacaaggc | 420 |
| ccacagggtc cctcaggccc agcaggacgc caaggtaagg ccggttccgt cggtgagacc | 480 |
| ggcaaggctg gtccagctgg cccagtaggt gcaaccggcc cggtaggtcc agccggtgcc | 540 |
| caaggccaaa ccggagccgc cggcccacga ggagcgcagg gaccacaggg ccccaagggt | 600 |
| gcgatgggac ccaagggcga ccaaggaccc aaggagagc aaggccagag aggtgaacaa | 660 |
| ggtgccgtgg gcgagaacgg cgcacctggc ccagccggag ccaagggagc gactggcgca | 720 |
| ccaggtccca agggagccca gggcgatacc ggagcacgag gtgaagatgg agtccgtgga | 780 |
| ccagctggcc ccaagggttt gaacggccag aaggagcga ccggaccagt aggtccagcc | 840 |
| ggcccaaagg gacgcaaggg tcgagtgatc ttcatggaca ccccatacaa gggagacaac | 900 |
| aagggagaca caagggcgg caacaagtac gacaacaagt acgacaacaa gtacgacaac | 960 |
| aagtacgaca acaagggcga caacaaggga caatcgtact aa | 1002 |

<210> SEQ ID NO 11
<211> LENGTH: 981
<212> TYPE: DNA
<213> ORGANISM: Nematus oligospilus

<400> SEQUENCE: 11

| | |
|---|---|
| atgagacaag tcagcttcct catcttcgcc gcagtggcgc tattcgtcgt cctgggcgcc | 60 |
| gatgcaagaa gcgttaaggg aggtaaatca ggcaagggct ccgtggaaa gagcggcgga | 120 |
| tacgacggtc gaaacaatgg aggaaacgac ggtggaaacg acggtggaga cggtgcgcta | 180 |
| gcctggatgc agggtccaat tggcaaggaa ggaccaatcg gtgagcgtgg cgcagccggt | 240 |
| cccaaaggtc cagtcggtca aactggcgcc gtcggtgata gaggcgcggt cggcgctcca | 300 |
| ggtcccaacg gtcgcactgg ttcagtcggt gtcaagggag ctcaaggtca acaaggtcca | 360 |
| tccggtccca gaggcgcaac aggcgccgca ggtccagcag gtccagcagg cccaaccgga | 420 |
| gagcaaggcg caaccggtgc cccggtgcc gccggtccca ccggaccacc tggactccag | 480 |
| ggtccacgcg gagcgaaggg agtccaagga gagaaggac acagggcgc ccagggcaac | 540 |
| agaggagcac caggcgtatc cggtcccaga ggaccaaccg gagaccgagg acaacaagga | 600 |

-continued

```
gccaagggcg acgtcggcgc caaaggcgca accggagctc caggtgccgc cggacccaga        660
ggtccgtcag gactgaaggg cgccaccggc aaccaggaca cagccggtcc agctggacag        720
gcgggagagg acgcggtgta cccatgggac aacaagggtt ccgacaacaa gggttacgac        780 aacaaggggtt acgacaacaa gggttccgac aacaaggggt acgacaacaa gggttacgac       840 aacaagggggt acgacaacaa gggttacgac aacaaggggtt acgacaacaa gggttacgac      900 aacaaggggtt acgataacaa gggttacgtc aacaaagatt acgacaacaa gggttacgac       960
aacaagggag agagttatta a                                                  981
```

<210> SEQ ID NO 12
<211> LENGTH: 915
<212> TYPE: DNA
<213> ORGANISM: Nematus oligospilus

<400> SEQUENCE: 12

```
agaagcgtta agggaggtaa atcaggcaag ggctccggtg aaagagcgg cggatacgac         60 ggtcgaaaca atggaggaaa cgacggtgga aacgacggtg gagacggtgc gctagcctgg       120
atgcagggtc caattggcaa ggaaggacca atcggtgagc gtggcgcagc cggtcccaaa       180
ggtccagtcg gtcaaactgg cgccgtcggt gatagaggcg cggtcggcgc tccaggtccc       240
aacggtcgca ctggttcagt cggtgtcaag ggagctcaag gtcaacaagg tccatccggt       300
cccagaggcg caacaggcgc cgcaggtcca gcaggtccag caggcccaac cggagagcaa       360
ggcgcaaccg gtgcccccgg tgccgccggt cccaccggac cacctggact ccagggtcca       420
cgcggagcga agggagtcca aggagagaag ggaccacagg gcgcccaggg caacagagga       480
gcaccaggcg tatccggtcc cagaggacca accggagacc gaggacaaca aggagccaag       540
ggcgacgtcg gcgccaaagg cgcaaccgga gctccaggtg ccgccggacc cagaggtccg       600
tcaggactga agggcgccac cggcaaccag ggaccagccg gtccagctgg acaggcggga       660
gaggacgcgg tgtacccatg ggacaacaag ggttccgaca caagggtta cgacaacaag       720 ggttacgaca caagggttc cgacaacaag ggtacgaca caagggtta cgacaacaag        780 gggtacgaca caagggtta cgacaacaag ggttacgaca caagggtta cgacaacaag        840 ggttacgata caagggtta cgtcaacaaa gattacgaca caagggtta cgacaacaag         900 ggagagagtt attaa                                                         915
```

<210> SEQ ID NO 13
<211> LENGTH: 180
<212> TYPE: PRT
<213> ORGANISM: Nematus oligospilus

<400> SEQUENCE: 13

Gly Pro Arg Gly Ala Asp Gly Lys Ile Gly Pro Ala Gly Pro Gln Gly
1               5                   10                  15

Pro Ser Gly Pro Ala Gly Pro Thr Gly Pro Val Gly Pro Arg Gly Asp
            20                  25                  30

Ala Gly Arg Pro Gly Ala Thr Gly Ala Thr Gly Pro Asp Gly Pro Lys
        35                  40                  45

Gly Glu Phe Gly Pro Gln Gly Pro Ser Gly Pro Arg Gly Ala Pro Gly
    50                  55                  60

Pro Gln Gly Pro Ala Gly Pro Thr Gly Arg Asp Gly Pro Lys Gly Ala
65                  70                  75                  80

Ala Gly Pro Ala Gly Ala Ala Gly Pro Ala Gly Ser Pro Gly Ala Gln

```
                85                  90                  95
Gly Glu Thr Gly Asp Arg Gly Asp Arg Gly Leu Lys Gly Asp Val Gly
            100                 105                 110

Ala Gln Gly Gly Lys Gly Ile Pro Gly Pro Ala Gly Pro Arg Gly Gln
        115                 120                 125

Thr Gly Pro Asn Gly Leu Pro Gly Ala Lys Gly Glu Thr Gly Pro Lys
    130                 135                 140

Gly Ala Gln Gly Pro Ala Gly Pro Ala Gly Pro Lys Gly Glu Asp Gly
145                 150                 155                 160

Ala Thr Gly Glu Thr Gly Pro Arg Gly Pro Ala Gly Pro Ala Gly Ala
                165                 170                 175

Ala Gly Lys Asp
            180

<210> SEQ ID NO 14
<211> LENGTH: 186
<212> TYPE: PRT
<213> ORGANISM: Nematus oligospilus

<400> SEQUENCE: 14

Gly Arg Val Gly Pro Ala Gly Glu Gln Gly Arg Gln Gly Pro Ala Gly
1               5                   10                  15

Pro Pro Gly Pro Val Gly Asp Arg Gly Gln Thr Gly Arg Ser Gly Gln
            20                  25                  30

Thr Gly Pro Gln Gly Pro Gln Gly Pro Ser Gly Pro Ala Gly Arg Gln
        35                  40                  45

Gly Lys Ala Gly Ser Val Gly Glu Thr Gly Lys Ala Gly Pro Ala Gly
    50                  55                  60

Pro Val Gly Ala Thr Gly Pro Val Gly Pro Ala Gly Ala Gln Gly Gln
65              70                  75                  80

Thr Gly Ala Ala Gly Pro Arg Gly Ala Gln Gly Pro Gln Gly Pro Lys
                85                  90                  95

Gly Ala Met Gly Pro Lys Gly Asp Gln Gly Pro Lys Gly Glu Gln Gly
            100                 105                 110

Gln Arg Gly Glu Gln Gly Ala Val Gly Glu Asn Gly Ala Pro Gly Pro
        115                 120                 125

Ala Gly Ala Lys Gly Ala Thr Gly Ala Pro Gly Pro Lys Gly Ala Gln
    130                 135                 140

Gly Asp Thr Gly Ala Arg Gly Glu Asp Gly Val Arg Gly Pro Ala Gly
145                 150                 155                 160

Pro Lys Gly Leu Asn Gly Gln Lys Gly Ala Thr Gly Pro Val Gly Pro
                165                 170                 175

Ala Gly Pro Lys Gly Arg Lys Gly Arg Val
            180                 185

<210> SEQ ID NO 15
<211> LENGTH: 180
<212> TYPE: PRT
<213> ORGANISM: Nematus oligospilus

<400> SEQUENCE: 15

Gly Pro Ile Gly Lys Glu Gly Pro Ile Gly Glu Arg Gly Ala Ala Gly
1               5                   10                  15

Pro Lys Gly Pro Val Gly Gln Thr Gly Ala Val Gly Asp Arg Gly Ala
            20                  25                  30

Val Gly Ala Pro Gly Pro Asn Gly Arg Thr Gly Ser Val Gly Val Lys
```

```
                35                  40                  45
Gly Ala Gln Gly Gln Gln Gly Pro Ser Gly Pro Arg Gly Ala Thr Gly
        50                  55                  60
Ala Ala Gly Pro Ala Gly Pro Ala Gly Pro Thr Gly Glu Gln Gly Ala
 65                  70                  75                  80
Thr Gly Ala Pro Gly Ala Ala Gly Pro Thr Gly Pro Pro Gly Leu Gln
                85                  90                  95
Gly Pro Arg Gly Ala Lys Gly Val Gln Gly Glu Lys Gly Pro Gln Gly
            100                 105                 110
Ala Gln Gly Asn Arg Gly Ala Pro Gly Val Ser Gly Pro Arg Gly Pro
            115                 120                 125
Thr Gly Asp Arg Gly Gln Gln Gly Ala Lys Gly Asp Val Gly Ala Lys
            130                 135                 140
Gly Ala Thr Gly Ala Pro Gly Ala Ala Gly Pro Arg Gly Pro Ser Gly
145                 150                 155                 160
Leu Lys Gly Ala Thr Gly Asn Gln Gly Pro Ala Gly Pro Ala Gly Gln
                165                 170                 175
Ala Gly Glu Asp
            180

<210> SEQ ID NO 16
<211> LENGTH: 278
<212> TYPE: PRT
<213> ORGANISM: Artificial Sequence
<220> FEATURE:
<223> OTHER INFORMATION: Type A collagen-like silk protein with signal
      sequence and C-terminal His tag

<400> SEQUENCE: 16

Met Arg Gln Val Ser Tyr Phe Ile Leu Ala Ala Val Ala Leu Phe Ala
  1               5                  10                  15
Ile Phe Ala Glu Ala Val Pro Val Ala Thr Pro Ser Lys Gly Ser Lys
                20                  25                  30
Ser Gly His Gly Gly Glu Ser Gly Asn Tyr Gly His Gly Gly Arg Gly
            35                  40                  45
Gly Asp Gly Ser Asp Gly Ala Gly Gly Val Gly Gly Gly Arg Ser
 50                  55                  60
Gly Gly Ser Gly Trp Ala Gly Pro Gln Gly Pro Arg Gly Ala Asp Gly
 65                  70                  75                  80
Lys Ile Gly Pro Ala Gly Pro Gln Gly Ser Gly Pro Ala Gly Pro
                85                  90                  95
Thr Gly Pro Val Gly Pro Arg Gly Asp Ala Gly Arg Pro Gly Ala Thr
            100                 105                 110
Gly Ala Thr Gly Pro Asp Gly Pro Lys Gly Glu Phe Gly Pro Gln Gly
            115                 120                 125
Pro Ser Gly Pro Arg Gly Ala Pro Gly Pro Gln Gly Pro Ala Gly Pro
            130                 135                 140
Thr Gly Arg Asp Gly Pro Lys Gly Ala Ala Gly Pro Ala Gly Ala Ala
145                 150                 155                 160
Gly Pro Ala Gly Ser Pro Gly Ala Gln Gly Glu Thr Gly Asp Arg Gly
                165                 170                 175
Asp Arg Gly Leu Lys Gly Asp Val Gly Ala Gln Gly Gly Lys Gly Ile
            180                 185                 190
Pro Gly Pro Ala Gly Pro Arg Gly Gln Thr Gly Pro Asn Gly Leu Pro
            195                 200                 205
```

```
Gly Ala Lys Gly Glu Thr Gly Pro Lys Gly Ala Gln Gly Pro Ala Gly
    210                 215                 220

Pro Ala Gly Pro Lys Gly Glu Asp Gly Ala Thr Gly Glu Thr Gly Pro
225                 230                 235                 240

Arg Gly Pro Ala Gly Pro Ala Gly Ala Gly Lys Asp Ile Ile Ile
                245                 250                 255

Trp Lys Gly Gln Lys Gly Trp Arg Ser Pro Ser Glu Arg Lys Ser Tyr
                260                 265                 270

His His His His His His
        275

<210> SEQ ID NO 17
<211> LENGTH: 358
<212> TYPE: PRT
<213> ORGANISM: Artificial Sequence
<220> FEATURE:
<223> OTHER INFORMATION: Type B collagen-like silk with signal sequence
      and C-terminal His tag

<400> SEQUENCE: 17

Met Arg Gln Ala Thr Phe Phe Ile Phe Ala Val Val Ala Val Phe Ala
1               5                   10                  15

Val Ala Gly Val Pro Val Pro Gly Asp Asp Gln Gly Arg Ala Glu Ser
                20                  25                  30

His Ala Ser Ala Ser Ser Ser Ala Ser Ala Gly Asn Gly Gly Asn Lys
            35                  40                  45

Gly Lys Ala Asp Ser Tyr Ala Glu Ala Asp Ser Tyr Ala Ser Ala Gly
    50                  55                  60

Asn Asp Gly Lys Thr Gly Asn Ala Gly Ser Tyr Ala Ala Ala Gly Ser
65                  70                  75                  80

Ser Ala Ser Ala Gly Asn Asp Gly Asn Ala Gly Ser Tyr Ala Ser Gly
                85                  90                  95

Asn Ser Tyr Ala Asn Ala Gly Asn Asp Gly Asn Arg Gly Asn Arg Gly
            100                 105                 110

Asp Asp Gly Gly Arg Arg Gly Gln Gly Trp Gly Arg Val Gly Pro Ala
        115                 120                 125

Gly Glu Gln Gly Arg Gln Gly Pro Ala Gly Pro Pro Gly Pro Val Gly
    130                 135                 140

Asp Arg Gly Gln Thr Gly Arg Ser Gly Gln Thr Gly Pro Gln Gly Pro
145                 150                 155                 160

Gln Gly Pro Ser Gly Pro Ala Gly Arg Gln Lys Ala Gly Ser Val
                165                 170                 175

Gly Glu Thr Gly Lys Ala Gly Pro Ala Gly Pro Val Gly Ala Thr Gly
            180                 185                 190

Pro Val Gly Pro Ala Gly Ala Gln Gly Thr Gly Ala Ala Gly Pro
        195                 200                 205

Arg Gly Ala Gln Gly Pro Gln Gly Pro Lys Gly Ala Met Gly Pro Lys
    210                 215                 220

Gly Asp Gln Gly Pro Lys Gly Glu Gln Gly Gln Arg Gly Glu Gln Gly
225                 230                 235                 240

Ala Val Gly Glu Asn Gly Ala Pro Gly Pro Ala Gly Ala Lys Gly Ala
                245                 250                 255

Thr Gly Ala Pro Gly Pro Lys Gly Ala Gln Gly Asp Thr Gly Ala Arg
            260                 265                 270

Gly Glu Asp Gly Val Arg Gly Pro Ala Gly Pro Lys Gly Leu Asn Gly
        275                 280                 285
```

```
Gln Lys Gly Ala Thr Gly Pro Val Gly Pro Ala Gly Pro Lys Gly Arg
        290                 295                 300

Lys Gly Arg Val Ile Phe Met Asp Thr Pro Tyr Lys Gly Asp Asn Lys
305                 310                 315                 320

Gly Asp Asn Lys Gly Asn Lys Tyr Asp Asn Lys Tyr Asp Asn Lys
                325                 330                 335

Tyr Asp Asn Lys Tyr Asp Asn Lys Gly Asp Asn Lys Gly Gln Ser Tyr
        340                 345                 350

His His His His His His
        355

<210> SEQ ID NO 18
<211> LENGTH: 429
<212> TYPE: PRT
<213> ORGANISM: Artificial Sequence
<220> FEATURE:
<223> OTHER INFORMATION: Type C collagen-like silk with N-terminal His
      tag followed by N-terminal V domain followed by thrombin cleavage
      site

<400> SEQUENCE: 18

Met Asn His Lys Val His Met His His His His Ala Asp Glu
1               5                   10                  15

Gln Glu Glu Lys Ala Lys Val Arg Thr Glu Leu Ile Gln Glu Leu Ala
            20                  25                  30

Gln Gly Leu Gly Gly Ile Glu Lys Lys Asn Phe Pro Thr Leu Gly Asp
        35                  40                  45

Glu Asp Leu Asp His Thr Tyr Met Thr Lys Leu Leu Thr Tyr Leu Gln
    50                  55                  60

Glu Arg Glu Gln Ala Glu Asn Ser Trp Arg Lys Arg Leu Leu Lys Gly
65                  70                  75                  80

Ile Gln Asp His Ala Leu Asp Leu Val Pro Arg Gly Ser Pro Gly His
                85                  90                  95

Met Arg Gln Val Ser Phe Leu Ile Phe Ala Ala Val Ala Leu Phe Val
            100                 105                 110

Val Leu Gly Ala Asp Ala Arg Ser Val Lys Gly Gly Lys Ser Gly Lys
        115                 120                 125

Gly Ser Gly Gly Lys Ser Gly Gly Tyr Asp Arg Asn Asn Gly Gly
130                 135                 140

Asn Asp Gly Gly Asn Asp Gly Gly Asp Gly Ala Leu Ala Trp Met Gln
145                 150                 155                 160

Gly Pro Ile Gly Lys Glu Gly Pro Ile Gly Glu Arg Gly Ala Ala Gly
                165                 170                 175

Pro Lys Gly Pro Val Gly Gln Thr Gly Ala Val Gly Asp Arg Gly Ala
            180                 185                 190

Val Gly Ala Pro Gly Pro Asn Gly Arg Thr Gly Ser Val Gly Val Lys
        195                 200                 205

Gly Ala Gln Gly Gln Gln Gly Pro Ser Gly Pro Arg Gly Ala Thr Gly
    210                 215                 220

Ala Ala Gly Pro Ala Gly Pro Ala Gly Pro Thr Gly Glu Gln Gly Ala
225                 230                 235                 240

Thr Gly Ala Pro Gly Ala Ala Gly Pro Thr Gly Pro Pro Gly Leu Gln
                245                 250                 255

Gly Pro Arg Gly Ala Lys Gly Val Gln Gly Glu Lys Gly Pro Gln Gly
            260                 265                 270
```

```
Ala Gln Gly Asn Arg Gly Ala Pro Gly Val Ser Gly Pro Arg Gly Pro
        275                 280                 285

Thr Gly Asp Arg Gly Gln Gln Gly Ala Lys Gly Asp Val Ala Pro Lys
    290                 295                 300

Ala Gln Pro Glu Arg Ala Lys Gly Ala Thr Gly Ala Pro Gly Ala Ala
305                 310                 315                 320

Gly Pro Arg Gly Pro Ser Gly Leu Lys Gly Ala Thr Gly Asn Gln Gly
                325                 330                 335

Pro Ala Gly Pro Ala Gly Gln Ala Gly Glu Asp Ala Val Tyr Pro Trp
            340                 345                 350

Asp Asn Lys Gly Ser Asp Asn Lys Gly Tyr Asp Asn Lys Gly Tyr Asp
        355                 360                 365

Asn Lys Gly Ser Asp Asn Lys Gly Tyr Asp Asn Lys Gly Tyr Asp Asn
    370                 375                 380

Lys Gly Tyr Asp Asn Lys Gly Tyr Asp Asn Lys Gly Tyr Asp Asn Lys
385                 390                 395                 400

Gly Tyr Asp Asn Lys Gly Tyr Asp Asn Lys Gly Tyr Val Asn Lys Asp
                405                 410                 415

Tyr Asp Asn Lys Gly Tyr Asp Asn Lys Gly Glu Ser Tyr
            420                 425
```

<210> SEQ ID NO 19
<211> LENGTH: 837
<212> TYPE: DNA
<213> ORGANISM: Artificial Sequence
<220> FEATURE:
<223> OTHER INFORMATION: ORF encoding type A fusion

<400> SEQUENCE: 19

```
atgcgtcagg ttagctattt tatcctggca gcagttgcac tgtttgcaat tttgcagaa     60 gcagttccgg ttgcaacccc gagcaaaggt agcaaaaagcg gtcatggtgg tgaaagcggt    120
aattatggtc atggtggccg tggtggtgat ggttctgatg gtggtgccgg tggtgttggt    180
ggtggtcgta gcggtggtag cggttgggca ggtccgcaag gtccgcgtgg tgcagatggt    240
aaaattggtc cggctggtcc gcagggtcct tctggtccgg caggtccaac aggtccggtg    300
ggtcctcgtg gtgatgcagg tcgtccgggt gcaaccggtg ctacaggtcc ggatggtccg    360
aaaggtgaat ttggtcctca gggtccgagc ggtccacgtg gtgcaccagg tccacagggt    420
cctgcaggtc ctaccggtcg tgatggtcct aaaggcgcag caggtccggc aggcgcagct    480
ggtcctgctg gttctccggg tgcacagggt gaaaccggtg atcgtggtga tcgcggtctg    540
aaaggtgatg ttggtgcgca gggtggtaaa ggtattccgg gtccggcagg acctcgtggt    600
cagaccggtc cgaatggtct gcctggtgca aaaggcgaaa ccggtccgaa aggcgctcaa    660
ggtccggctg gccctgccgg tcctaaaggt gaagatggtg ccaccggtga aacaggtcct    720
cgtggccctg caggtccagc cggtgcagca ggtaaagata ttatcatttg gaaaggtcag    780
aaaggttggc gtagcccgag cgaacgtaaa agctatcatc atcatcacca tcattaa       837
```

<210> SEQ ID NO 20
<211> LENGTH: 1077
<212> TYPE: DNA
<213> ORGANISM: Artificial Sequence
<220> FEATURE:
<223> OTHER INFORMATION: ORF encoding type B fusion

<400> SEQUENCE: 20

```
atgcgtcagg ccaccttttt tatttttgcc gttgttgcag tttttgcagt tgccggtgtt     60
```

```
ccggttccgg gtgatgatca gggtcgtgca gaaagccatg caagcgcaag cagcagcgca        120
tctgccggta atggtggtaa taaaggcaaa gcagatagct atgcagaagc tgatagctac        180
gcaagcgcag gcaatgatgg taaaaccggt aatgccggta gctatgcagc agcgggtagc        240
agcgcctcag cgggtaatga tggcaatgcc ggttcttatg caagcggtaa tagctatgca        300
aatgccggta acgatggtaa tcgcggtaat cgtggtgatg atggtggtcg tcgtggtcag        360
ggttggggtc gtgttggtcc tgcaggcgaa caaggtcgtc agggtccggc tggtccgcct        420
ggtcctgttg gtgatcgtgg tcagaccggt cgtagcggtc agacaggtcc gcagggtcca        480
cagggtccgt caggtccagc aggccgtcaa ggtaaagccg gtagcgttgg tgaaaccggt        540
aaagcgggtc cggcaggacc ggttggtgca acgggtccgg tgggtcctgc tggtgcacag        600
ggccagacgg gtgcagctgg tccgcgtggt gctcaaggtc cgcagggacc gaaaggtgca        660
atgggtccta aggtgatca gggtcctaaa ggtgaacaag gtcagcgtgg tgaacagggt        720
gcagttggtg aaaatggtgc accgggacct gccggtgcca aggagcaac gggagcacct        780 ggtccgaaag gcgcacaggg tgataccggt gcacgcggtg aagatggtgt tcgtggtccg        840
gctggcccta aggtctgaa tggtcagaaa ggtgccacag gtccggttgg ccctgccggt        900
ccaaaaggtc gtaaaggtcg cgttattttc atggatatcc gtataaagg tgataacaaa        960 ggcgataata aggtggcaa caaatatgat aacaaatacg acaataaata cgacaacaaa       1020
tatgataata aggtgacaa taaaggccag agctaccacc accatcacca tcattaa        1077

<210> SEQ ID NO 21
<211> LENGTH: 1290
<212> TYPE: DNA
<213> ORGANISM: Artificial Sequence
<220> FEATURE:
<223> OTHER INFORMATION: ORF encoding type C fusion

<400> SEQUENCE: 21
atgaatcaca aagtgcatat gcatcaccat caccatcacg ctgatgaaca agaagagaaa         60
gctaaagtta gaactgaatt aattcaagag ttagctcagg gactagggg tattgagaaa        120 aaaaattttc aactctagg tgatgaagat ttagatcata cttatatgac aaagctatta        180
acatacctac aggaacgaga acaagctgag aatagttggc gaaaaagact actaaagggt        240
atacaagatc atgcccttga tctggtgcca cgcggtagtc ccgggcatat gagacaagtc        300
agcttcctca tcttcgccgc agtggcgcta ttcgtcgtcc tgggcgccga tgcaagaagc        360
gttaagggag gtaaatcagg caagggctcc ggtggaaaga gcggcggata cgacggtcga        420
aacaatggag gaaacgacgg tggaaacgac ggtggagacg gtgcgctagc ctggatgcag        480
ggtccaattg gcaaggaagg accaatcggt gagcgtggcg cagccggtcc caaaggtcca        540
gtcggtcaaa ctggcgccgt cggtgataga ggcgcggtcg gcgctccagg tcccaacggt        600
cgcactggtt cagtcggtgt caagggagct caaggtcaac aaggtccatc cggtcccaga        660
ggcgcaacag gcgccgcagg tccagcaggt ccagcaggcc caaccggaga gcaaggcgca        720
accggtgccc ccggtgccgc cggtcccacc ggaccacctg gactccaggg tccacgcgga        780
gcgaagggag tccaaggaga aagggaccc cagggcgccc agggcaacag aggagcacca        840
ggcgtatccg gtcccagagg accaaccgga gaccgaggac aacaaggagc caagggcgac        900
gtcgcgccaa aggcgcaacc ggagcgcgcc aaaggcgcaa ccggagctcc aggtgccgcc        960
ggacccagag gtccgtcagg actgaagggc gccaccggca accagggacc agccggtcca       1020
```

| | |
|---|---|
| gctggacagg cgggagagga cgcggtgtac ccatgggaca acaagggttc cgacaacaag | 1080 |
| ggttacgaca acaagggtta cgacaacaag ggttccgaca acaagggtta cgacaacaag | 1140 |
| ggttacgaca acaaggggta cgacaacaag ggttacgaca acaagggtta cgacaacaag | 1200 |
| ggttacgaca acaaggasta cgataacaag ggttacgtca acaaagatta cgacaacaag | 1260 |
| ggttacgaca acaagggaga gagttattaa | 1290 |

```
<210> SEQ ID NO 22
<211> LENGTH: 756
<212> TYPE: DNA
<213> ORGANISM: Artificial Sequence
<220> FEATURE:
<223> OTHER INFORMATION: Codon optimized ORF type A for bacterial
      expression (without signal)

<400> SEQUENCE: 22
```

| | |
|---|---|
| gttccggttg caaccccgag caaaggtagc aaaagcggtc atggtggtga agcggtaat | 60 |
| tatggtcatg gtggccgtgg tggtgatggt tctgatggtg gtgccggtgg tgttggtggt | 120 |
| ggtcgtagcg gtggtagcgg ttgggcaggt ccgcaaggtc cgcgtggtgc agatggtaaa | 180 |
| attggtccgg ctggtccgca gggtcctttc ggtccggcag gtccaacagg tccggtgggt | 240 |
| cctcgtggtg atgcaggtcg tccgggtgca accggtgcta caggtccgga tggtccgaaa | 300 |
| ggtgaatttg gtcctcaggg tccgagcggt ccacgtggtg caccaggtcc acagggtcct | 360 |
| gcaggtccta ccggtcgtga tggtcctaaa ggcgcagcag gtccggcagg cgcagctggt | 420 |
| cctgctggtt ctccgggtgc acagggtgaa accggtgatc gtggtgatcg cggtctgaaa | 480 |
| ggtgatgttg gtgcgcaggg tggtaaaggt attccgggtc cggcaggacc tcgtggtcag | 540 |
| accggtccga tggtctgcc tggtgcaaaa ggcgaaaccg gtccgaaagg cgctcaaggt | 600 |
| ccggctggcc ctgccggtcc taaaggtgaa gatggtgcca ccggtgaaac aggtcctcgt | 660 |
| ggccctgcag gtccagccgg tgcagcaggt aaagatatta tcatttggaa aggtcagaaa | 720 |
| ggttggcgta gcccgagcga acgtaaaagc tattaa | 756 |

```
<210> SEQ ID NO 23
<211> LENGTH: 1002
<212> TYPE: DNA
<213> ORGANISM: Artificial Sequence
<220> FEATURE:
<223> OTHER INFORMATION: Codon optimized ORF for type B bacterial
      expression (without signal)

<400> SEQUENCE: 23
```

| | |
|---|---|
| gttccggttc cgggtgatga tcagggtcgt gcagaaagcc atgcaagcgc aagcagcagc | 60 |
| gcatctgccg gtaatggtgg taataaaggc aaagcagata gctatgcaga agctgatagc | 120 |
| tacgcaagcg caggcaatga tggtaaaacc ggtaatgccg gtagctatgc agcagcgggt | 180 |
| agcagcgcct cagcgggtaa tgatggcaat gccggttctt atgcaagcgg taatagctat | 240 |
| gcaaatgccg gtaacgatgg taatcgcggt aatcgtggtg atgatggtgg tcgtcgtggt | 300 |
| cagggttggg gtcgtgttgg tcctgcaggc gaacaaggtc gtcagggtcc ggctggtccg | 360 |
| cctggtcctg ttggtgatcg tggtcagacc ggtcgtagcg gtcagacagg tccgcagggt | 420 |
| ccacagggtc cgtcaggtcc agcaggccgt caaggtaaag ccggtagcgt tggtgaaacc | 480 |
| ggtaaagcgg gtccggcagg accggttggt gcaacgggtc cgtgggtcc tgctggtgca | 540 |
| cagggccaga cgggtgcagc tggtccgcgt ggtgctcaag gtccgcaggg accgaaaggt | 600 |
| gcaatgggtc ctaaaggtga tcagggtcct aaaggtgaac aaggtcagcg tggtgaacag | 660 |

```
ggtgcagttg gtgaaaatgg tgcaccggga cctgccggtg ccaaaggagc aacgggagca    720
cctggtccga aaggcgcaca gggtgatacc ggtgcacgcg gtgaagatgg tgttcgtggt    780
ccggctggcc ctaaaggtct gaatggtcag aaaggtgcca caggtccggt tggccctgcc    840
ggtccaaaag gtcgtaaagg tcgcgttatt ttcatggata ccccgtataa aggtgataac    900
aaaggcgata ataaaggtgg caacaaatat gataacaaat acgacaataa atacgacaac    960
aaatatgata ataaaggtga caataaaggc cagagctact aa                     1002
```

COLLAGEN-LIKE SILK GENES

CROSS-REFERENCE TO RELATED APPLICATIONS

This application is a national phase application of PCT/AU2012/001412, filed Nov. 15, 2012, which application claims priority benefit of U.S. application Ser. No. 61/560,649, filed Nov. 16, 2011.

FIELD OF THE INVENTION

The present invention relates to silk proteins which can be used to produce silk with a collagen-like structure, as well as nucleic acids encoding such proteins. The present invention also relates to recombinant cells and/or organisms which synthesize silk proteins. Silk proteins of the invention can be used for a variety of purposes such as in the production of personal care products, plastics, textiles, and biomedical products.

BACKGROUND OF THE INVENTION

'Silk' has become a single, all encompassing description for an extremely wide range of biological materials (Sutherland et al., 2010) that are an ancient product in evolution. Silks are produced by a wide range insects, for example by the larvae of insects where a cocoon is formed for protection during metamorphosis, by adult insects such as webspinners that spin silk with structures on their front legs to make a web-like pouch or gallery in which they live, in the Hymenoptera (which includes bees, wasps and ants) where silk is part of nest construction, and by large numbers of other arthropods, most notably the various arachnids such as spiders where orb-webs used for catching prey are common (Sutherland et al., 2010).

Silks are fibrous protein secretions that exhibit exceptional strength and toughness and as such have been the target of extensive study. Silks are produced by over 30,000 species of spiders and by many insects. Furthermore, in comparison with other arthropods, spiders produce more than one silk type, typically between 5 and 7, each with different properties for different purposes, with most involved with web construction. Of these the major ampullate silk, also known as the 'dragline silk' which is used as a lifeline and for the web's outer rim and spokes has attracted much attention since it can be as strong per unit weight as steel, but much tougher.

Despite the diversity of structures and distributions, silks have features in common, notably, being semicrystalline materials, that is materials with regions of ordered molecular structure (crystallites) within an amorphous matrix and also, all show typically similar protein compositions, often rich in alanine, serine, and/or glycine (Sutherland et al., 2010).

Overall, very few of these silks have been characterised, with most research concentrating on the cocoon silk of the domesticated silkworm, *Bombyx mori* and on the dragline silks of the orb-weaving spider *Nephila clavipes*, the European garden spider, *Araneus diadematus*, and the nursery web spider, *Euprosthenops australis*.

In the Lepidoptera and spider, the fibroin silk genes code for proteins that are generally large with prominent hydrophilic terminal domains at either end spanning an extensive region of alternating hydrophobic and hydrophilic blocks (Bini et al., 2004). Generally these proteins comprise different combinations of crystalline arrays of β-pleated sheets loosely associated with β-sheets, β-spirals, α-helices and amorphous regions (see Craig and Riekel, 2002 for review).

The ready commercial availability of domesticated silk worm, *B. mori*, silk, has meant that there is no commercial driver to make a recombinant silkworm silk, especially considering the difficulties in making a recombinant product for a protein that is so large and is built around a highly repetitive structure. This silk comprises 2 chains; a heavy chain of ~390 kDa and a light chain of ~26 kDa in a 1:1 ratio, with these 2 chains linked by a critical disulphide bond.

Very limited complete sequence data is available for spider silks. This is because of the difficulties in studying highly repetitive structures (Arcidiacono et al., 1998). The main examples include dragline silk from black widow spider (Ayoub et al., 2007) and flagelliform silk from *Nephila clavipes* (Hayashi and Lewis, 2000). Whereas cultivation has proved highly successful for cocoon silks, farming is not an option for spider silks. The main problem is that most spiders are very territorial, aggressive and are cannibals. This has meant, however, that these have been considerable efforts to use recombinant technologies to produce spider silks. Native spider dragline silk is remarkably strong, although dragline silks from different species show different properties, examples exist of silks that are five times stronger by weight than steel, and/or three times tougher than Kevlar (Dupont) (Gosline et al., 1999, Volrath and Knight, 2001). All dragline silks have a high MW, 250-320 kDa (Ayoub et al., 2007), which on its own provides difficulties for recombinant expression. Dragline silks are typically composed of two main proteins, the major ampulate spidroins.

Spidroins have highly repetitive structures; they are modular, and contain hundreds of tandem repeats of distinct consensus motifs. MaSp1 spidroins generally comprise two motifs, polyalanine, and GlyGlyXaa, where Xaa is frequently Leu, Tyr, Gln or Ala. MaSp2 spidroins also contain polyalanine, as well as GlyProGlyXaaXaa repeats, where Xaa is frequently Gly, Gln or Tyr. The polyalanine or poly(glycyl-alanine) sequences form into tightly packed β-sheet crystallites.

More recently, a novel structural silk from the honey bee, *Apis melifera*, has attracted attention. Early X-ray evidence (Rudall, 1962) and different amino acid composition suggested that distinct class of silk molecule with an alpha helical structure was present in honeybee silk. Further analysis suggested that a four-stranded coiled-coil was present (Atkins, 1967). Recent molecular studies have confirmed this (Sutherland et al., 2006). Four silk genes have been identified (AmelFibroin 1-4), that each comprising a single exon with the genes separated by short regions of 1659-1796 bases are clustered sequentially in the *A. melifera* genome. They do not contain the highly repetitive sequences of other silks. Hence the chains are of a size and structure that can be more readily produced by recombinant methods. Honeybee silk may be useful as a new biomedical material. For example, it can be electrospun into sheets with uniform fibres of around 200 nm.

As silk fibres represent some of the strongest natural fibres known, they have been a subject to extensive research in attempts to reproduce their synthesis. However, a recurrent problem with expression of Lepidopteran and spider fibroin genes has been low expression rates in various recombinant expression systems due to the combination of repeating nucleotide motifs that lead to deleterious recombination events, large gene size and the small number of codons for each amino acid which leads to depletion of tRNA pools. Recombinant expression leads to difficulties during translation such as translational pauses as a result of codon preferences and codon demands and extensive recombination rates leading to truncation of the genes. Shorter, less repetitive sequences would avoid many of the problems associated with silk gene expression to date.

Silks have long found applications as biomedical materials, as they are typically biocompatible, biodegradable and have low immunogenicity. For biomedical applications, recombinant silk can be fabricated into various formats. Included in these is fabrication of a natural fibre, as well as hydrogels formed using connectivity through either physical or chemical crosslinking. Variations in properties can also be produced to match specific clinical needs, so that silks that can be produced for application that need high stress prior to failure, or where extensibility is required, such as in blood vessels, and where an appropriate modulus is required to modify or control cell response, for example for tissue engineering (Vepari and Kaplan, 2007). For example, this silk has been used to form non-woven mats (Dal Pra et al., 2004), and has been electrospun into fibres and fibre mats with fibre sizes from nanometers to microns (Jin et al., 2002). Silk fibroin films can be cast from aqueous and non-aqueous solvents (Minoura et al., 1990). Porous sponges can be made from silk solutions, for example, by using salt or sugar as porogens with fibroin in HFIP (Nazarov et al., 2004) or in fully aqueous system (Kim et al., 2005).

In the early 1960s, the silk of some sawflies (Hymenopteran) was suggested to have a collagen structure by X-ray diffraction patterns obtained cocoons or from silk fibres drawn from the salivary gland of *Nematus ribesii* (Rudall 1967 and 1968; Lucas and Rudall, 1968). The X-ray diffraction patterns suggest twisted cables of collagen molecules with dimensions of 30 A diameter—suggesting a two or three stranded cable (Rudall, 1967 and 1968). Proteins with X-ray diffraction patterns characteristic of collagen were also found in the silk gland of other species within the tribe Nematini: in *Hemichroa, Pristiphora, Pachynemalus, Pikonema* and *Nematus* species (subfamily Nematinae); in the anterior half of the silk gland of *Tomostethus* and *Tethida* species (subfamily Blennocampinae) (Rudall and Kenchington, 1971).

After the contents of the silk gland of *Nematus ribesii* were dissolved in 0.2M borate buffer and then precipitated in ethanol, the following amino acid analysis (from 4 different preps) was obtained (Gly: 336 (std dev=16); Ala: 122 (2); Ser: 33 (12); Pro: 100 (3); Hydroxy-Lys: 37 (3); Lys: 14 (4): Rudall and Kenchington, 1971). This analysis indicated that the silk had a high Gly content, characteristic of collagens, along with a high Ala content. However, these amino acids are also found in high abundance in cocoon and spider silks.

Considering the unique properties of silks produced by insects, and that they are available naturally in only minute amounts, there is a need for the identification of further novel nucleic acids encoding silk proteins.

SUMMARY OF THE INVENTION

The present inventors have identified numerous polynucleotides encoding silk proteins which are distinct from other silk proteins that have been characterized at the primary amino acid sequence level.

Thus, in a first aspect the present invention provides an isolated and/or exogenous polynucleotide which encodes a collagen-like silk polypeptide.

In an embodiment, the polynucleotide comprises one or more of:
i) a sequence of nucleotides as provided in any one of SEQ ID NO's 7 to 12, 22 or 23;
ii) a sequence of nucleotides encoding a polypeptide comprising an amino acid sequence as provided in any one of SEQ ID NO's 1 to 6;
iii) a sequence of nucleotides encoding a polypeptide comprising an amino acid sequence which is at least 30% identical to any one or more of SEQ ID NO's 1 to 6;
iv) a sequence of nucleotides encoding a biologically active fragment of ii) or iii),
v) a sequence of nucleotides which is at least 30% identical to any one or more of SEQ ID NO's 7 to 12, 22 or 23, or
vi) a sequence which hybridizes to any one or more of i) to v) under stringent conditions.

More preferably, the polynucleotide comprises a sequence of nucleotides encoding a polypeptide comprising an amino acid sequence which is at least 95% identical to any one or more of SEQ ID NO's 1 to 6.

In a particularly preferred embodiment, the polynucleotide encodes a polypeptide of the invention.

In another aspect, the present invention provides a vector comprising at least one polynucleotide of the invention.

In a preferred embodiment, the vector is an expression vector. More preferably, the polynucleotide is operably linked to a promoter in the expression vector.

In a further aspect, the present invention provides a host cell comprising at least one polynucleotide of the invention, and/or at least one vector of the invention.

The host cell can be any cell type. Examples include, but are not limited to, a bacterial, yeast, animal or plant cell. In a preferred embodiment, the cell is a bacterial cell.

In a further aspect, the present invention provides a substantially purified and/or recombinant collagen-like silk polypeptide.

In an embodiment, the polypeptide comprises one or more of:
i) an amino acid sequence as provided in any one of SEQ ID NO's 1 to 6;
ii) an amino acid sequence which is at least 30% identical to any one or more of SEQ ID NO's 1 to 6; or
iii) a biologically active fragment of i) or ii).

In an embodiment, the collagen-like silk polypeptide has, or is capable of forming under suitable conditions, a triple helical structure.

Preferably, the polypeptide can be purified from a species of Hymenoptera.

Preferably, the Genera of Hymenoptera is a species of *Hemichroa, Pristiphora, Pachynemalus, Pikonema, Tomostethus, Tethida* or *Nematus* (such as *Nematus ribesii* or *Nematus oligospilus*).

In a further embodiment, the polypeptide is fused to at least one other polypeptide. In a preferred embodiment, the at least one other polypeptide is selected from the group consisting of: a polypeptide that enhances the stability of a polypeptide of the present invention, a polypeptide that assists in the purification of the fusion protein, a polypeptide which promotes the formation of a triple helix, and a polypeptide which assists in the polypeptide of the invention being secreted from a cell (for example secreted from a bacterial cell). Examples of such fusion proteins are provided as SEQ ID NO's 16 to 18.

In yet another aspect, the present invention provides a non-human transgenic organism comprising an exogenous polynucleotide of the invention, the polynucleotide encoding at least one polypeptide according of the invention.

In an embodiment, the transgenic organism is a plant or transgenic non-human animal.

Also provided is a process for preparing a polypeptide of the invention, the process comprising cultivating one or more of a host cell of the invention, a vector of the invention, a transgenic organism of the invention, under conditions which allow expression of the polynucleotide encoding the polypeptide, and recovering the expressed polypeptide. As the skilled person would appreciate, the cultivation of a vector in an expression system is also known as cell-free expression.

Mammalian collagen to mimic the natural protein needs to be co-expressed with a prolyl-4-hydroxylase. Co-expression of prolyl-4-hydroxylase has been very problematic in bacteria, with the typical expression being achieved in yeast, especially *Pichia*. However, *Pichia* needs methanol for induction, which in the presence of added oxygen to get proper hydroxylation means that fermentation requires a flame-proof system. Thus, in a preferred embodiment, a process for preparing a polypeptide of the invention does not comprise the expression/presence of a prolyl-4-hydroxylase.

In a further embodiment, the process further comprises producing a product from the polypeptides such as a personal care product, textiles, plastics, or a biomedical product.

In another aspect, the present invention provides an isolated and/or recombinant antibody which specifically binds a polypeptide of the invention.

In another aspect, the present invention provides a silk fibre, sponge, film, hydrogel or particle comprising at least one polypeptide of the invention.

Preferably, the polypeptide is a recombinant polypeptide.

In a further aspect, the present invention provides a copolymer comprising at least two polypeptides of the invention.

Preferably, the polypeptides are recombinant polypeptides.

In another aspect, the present invention provides a product comprising one or more of at least one polypeptide of the invention, at least one silk fibre, sponge, film, hydrogel or particle of the invention, or at least one copolymer of the invention.

Examples of products of the invention include, but are not limited to, a personal care product, textiles, plastics, and biomedical products.

In an embodiment, at least some of the polypeptides in the silk fibre, sponge, film, hydrogel, particle, copolymer, or product of the invention are crosslinked.

In a preferred embodiment, a product of the invention is not a product, such as a cocoon, produced by an insect such as a sawfly.

In a further aspect, the present invention provides a composition comprising one or more of at least one polypeptide of the invention, at least one silk fibre, sponge, film, hydrogel or particle of the invention, or at least one copolymer of the invention, and one or more acceptable carriers.

In an embodiment, the composition further comprises a drug.

In another embodiment, the composition is for use as a medicine, a medical device or a cosmetic.

In yet another aspect, the present invention provides a composition comprising at least one polynucleotide of the invention, and one or more acceptable carriers.

In a further aspect, the present invention provides a process for producing a product comprising collagen-like silk polypeptides, the process comprising;
 i) obtaining collagen-like silk polypeptides, and
 ii) processing the polypeptides to produce the product.

As the skilled person will appreciate, the nature of the processing step will depend upon the form of the final product and the processing step can take a large number of different forms well within the capabaility of the skilled reader. For example, a product comprising silk fibres may be produced through spinning the polypeptides to produce the fibres and then weaving the fibres to produe the product.

Typically, the collagen-like silk polypeptides will be obtained by performing a process for preparing a polypeptide of the invention, or from a third party who has performed this process.

In a further aspect, the present invention provides a method of treating or preventing a disease, the method comprising administering a composition comprising one or more of at least one drug for treating or preventing the disease and a pharmaceutically acceptable carrier, wherein the pharmaceutically acceptable carrier is selected from at least one polypeptide of the invention, at least one silk fibre, sponge, film, hydrogel or particle of the invention, at least one copolymer of the invention, at least one product of the invention, or at least one composition of the invention.

Also provided is the use of one or more of at least one polypeptide of the invention, at least one silk fibre, sponge, film, hydrogel or particle of the invention, at least one copolymer of the invention, at least one product of the invention, or at least one composition of the invention, and at least one drug, for the manufacture of a medicament for treating or preventing a disease.

Furthermore, provided is the use of one or more of at least one polypeptide of the invention, at least one silk fibre, sponge, film, hydrogel or particle of the invention, at least one copolymer of the invention, at least one product of the invention, or at least one composition of the invention, and at least one drug, as a medicament for treating or preventing a disease.

In yet another aspect, the present invention provides a kit comprising one or more of at least one polypeptide of the invention, at least one polynucleotide of the invention, at least one vector of the invention, at least one silk fibre, sponge, film, hydrogel or particle of the invention, at least one copolymer of the invention, at least one product of the invention, or at least one composition of the invention.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Alignment of the collagen-like domains using the ExPASy (ETH) program (SEQ ID NOs: 13 to 15).

FIG. 2. Coomassie Blue stained SDS PAGE gels of sawfly silk protein expression. MW: molecular weight markers; A: expression of cDNA SF21; B: expression of SF9 cDNA; C: expression of V-SF30 cDNA.

Figure 3:
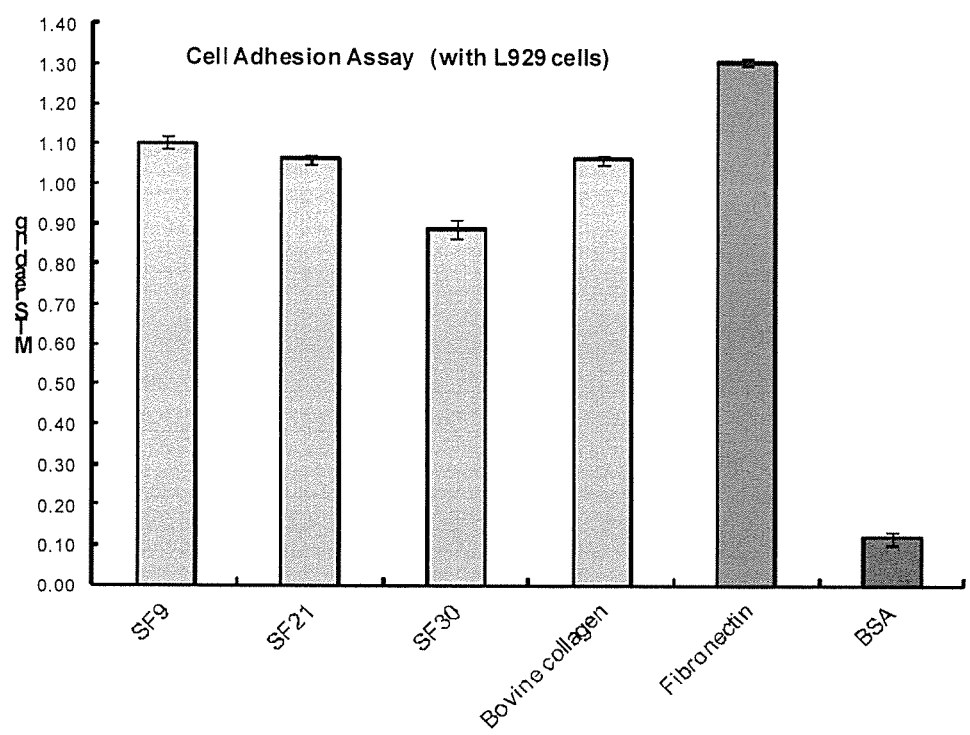

FIG. 3. Binding of SF9, SF21, SF30, bovine collagen and fibronectin to fibroblasts.

Figure 4:
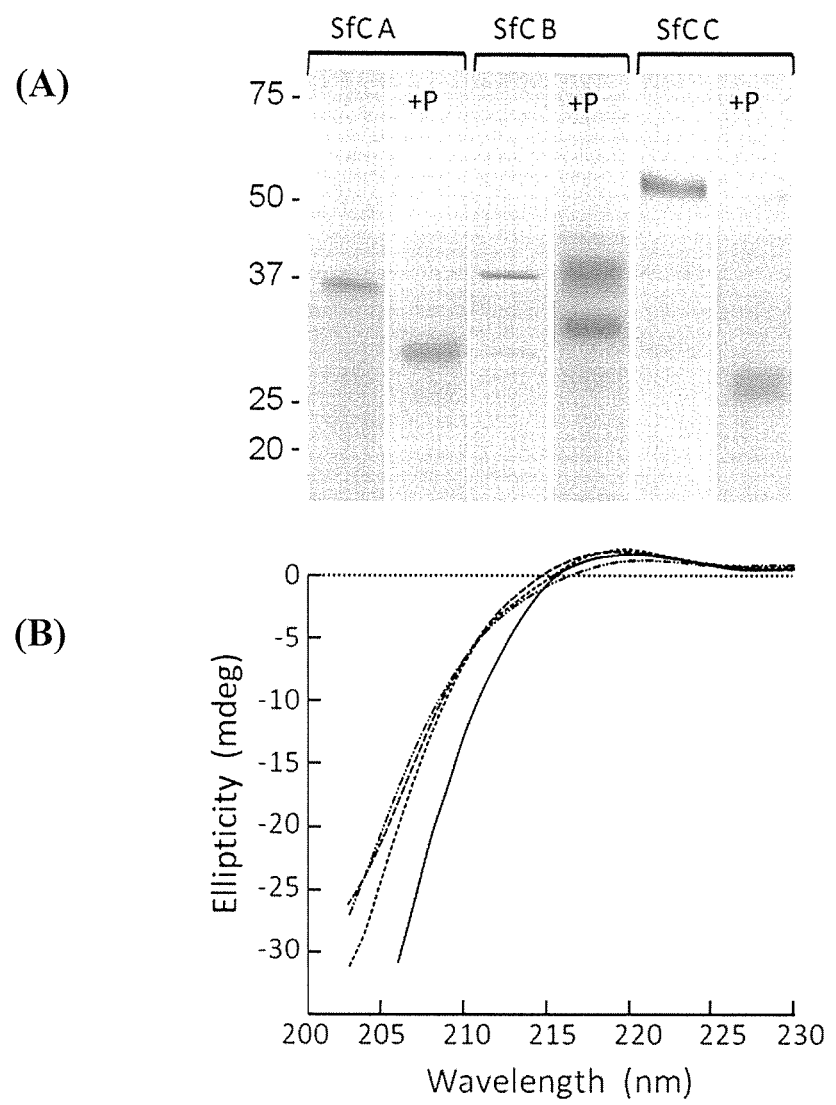

FIG. 4. Biophysical evidence that recombinant sawfly silk proteins are collagen. Top (A) Full length and pepsin resistant (+P) fragments of each silk protein after SDS PAGE separation. Incomplete digestion was observed for the SfC B chain. Molecular weight standards (kDa) are indicated on the left. (B) circular dichroism spectra of purified recombinant sawfly cocoon collagens after pepsin treatment showing characteristic collagen maxima at about 220 nm, SfC A (- - - -), SfC B (- . . - . . ) and SfC C (- - -). The solid line (-) shows a representative collagen spectra.

KEY TO THE SEQUENCE LISTING

SEQ ID NO:1—Sawfly collagen-like silk polypeptide type A sequence.
SEQ ID NO:2—Sawfly collagen-like silk polypeptide type A sequence without signal sequence.
SEQ ID NO:3—Sawfly collagen-like silk polypeptide type B sequence.
SEQ ID NO:4—Sawfly collagen-like silk polypeptide type B sequence without signal sequence.
SEQ ID NO:5—Sawfly collagen-like silk polypeptide type C sequence.
SEQ ID NO:6—Sawfly collagen-like silk polypeptide type C sequence without signal sequence.
SEQ ID NO:7—Open reading frame encoding sawfly collagen-like silk polypeptide type A sequence.
SEQ ID NO:8—Open reading frame encoding sawfly collagen-like silk polypeptide type A sequence without signal sequence.
SEQ ID NO:9—Open reading frame encoding sawfly collagen-like silk polypeptide type B sequence.
SEQ ID NO:10—Open reading frame encoding sawfly collagen-like silk polypeptide type B sequence without signal sequence.
SEQ ID NO:11—Open reading frame encoding sawfly collagen-like silk polypeptide type C sequence.
SEQ ID NO:12—Open reading frame encoding sawfly collagen-like silk polypeptide type C sequence without signal sequence.
SEQ ID NO:13—Collagen-like domain of type A silk protein (FIG. 1).
SEQ ID NO:14—Collagen-like domain of type B silk protein (FIG. 1).
SEQ ID NO:15—Collagen-like domain of type C silk protein (FIG. 1).
SEQ ID NO:16—Type A collagen-like silk fusion protein (Example 2).
SEQ ID NO:17—Type B collagen-like silk fusion protein (Example 2).
SEQ ID NO:18—Type C collagen-like silk fusion protein (Example 2).
SEQ ID NO:19—Open reading frame encoding SEQ ID NO:16.
SEQ ID NO:20—Open reading frame encoding SEQ ID NO:17.
SEQ ID NO:21—Open reading frame encoding SEQ ID NO:18.
SEQ ID NO:22—Codon optimized open reading frame type A for bacterial expression (without signal).
SEQ ID NO:23—Codon optimized open reading frame type B for bacterial expression (without signal).

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, recombinant biology, silk technology, immunology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning. A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning. Furthermore, a list or features including the phrase "and/or" between the second last and last feature means that any one or more the listed features may be present in any combination.

As used herein, the term about, unless stated to the contrary, refers to +/−20%, more preferably +/−10%, more preferably +/−5%, more preferably +/−1%, of the designated value.

As used herein, the terms "silk protein" and "silk polypeptide" refer to a fibrous protein/polypeptide that can be used to produce a silk fibre, and/or a fibrous protein complex.

Collagen is a group of naturally occurring proteins found in animals, especially in the flesh and connective tissues of mammals. It is the main component of connective tissue, and is the most abundant protein in mammals, making up about 25% to 35% of the whole-body protein content. In mammals, including human, there are 29 defined types, each with a different structure (composition) and function. Collagen, in the form of elongated fibrils, is mostly found in fibrous tissues such as tendon, ligament and skin. Collagen is a composed of a triple helix, which often exists as two identical chains (α1) and an additional chain that differs slightly in its chemical composition (α2). The amino acid composition of collagen is atypical for proteins, particularly with respect to its high hydroxyproline content. The most common motifs in the amino acid sequence of collagen are Glycine-X-Hydroxyproline and Glycine-Proline-Y, where X and Y can be any amino acid, although preferences exist for certain combinations (Ramshaw et al., 1998). As used herein, the term "collagen-like" refers to a polypeptide comprising Gly-X-Y triplets, where X and Y can be any amino acid. A silk protein of the invention could also be referred to as a "collagen silk" protein. In a particularly preferred embodiment, unlike collagen, a collagen-like silk protein of the invention does not have any hydroxyproline. Preferably, collagen-like silk proteins of the invention comprise at least about 40, more preferably at least about 50, Gly-X-Y triplets. Furthermore, preferably the Gly-X-Y triplets constitute at least about 40%, more preferably at least about 50%, of the primary amino acid sequence of the proteins. In an embodiment, a collagen-like silk polypeptide of the invention has, or is capable of forming under suitable conditions, a triple helical structure. In an embodiment, a collagen-like silk protein of the invention is resistant to trypsin digestion.

As used herein, a "silk fibre" refers to filaments comprising proteins of the invention which can be woven into various items such as textiles. This term excludes naturally occurring silk fibres such as cocoons of insects.

As used herein, a "copolymer" is a composition comprising two or more different silk proteins (for example type A and type B collagen-like silk proteins defined herein) of the invention. This term excludes naturally occurring copolymers such as cocoons of insects.

As used herein, the term "at least one" when referring to, for example, a polypeptide in a silk fibre of the invention clearly does not mean the silk fibre comprises only a single polypeptide molecule, but means that a homogeneous population of the polypeptides are present (for example type A collagen-like silk proteins) and other related molecules of the invention (such as type B and/or type C collagen-like silk proteins) are absent.

The term "plant" includes whole plants, vegetative structures (for example, leaves, stems, roots), floral organs/structures, seed (including embryo, endosperm, and seed coat), plant tissue (for example, vascular tissue, ground tissue, and the like), cells and progeny of the same.

A "transgenic plant" refers to a plant that contains a gene construct ("transgene") not found in a wild-type plant of the same species, variety or cultivar. A "transgene" as referred to herein has the normal meaning in the art of biotechnology and includes a genetic sequence which has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

"Polynucleotide" refers to an oligonucleotide, nucleic acid molecule or any fragment thereof. It may be DNA or RNA of genomic or synthetic origin, double-stranded or single-stranded, and combined with carbohydrate, lipids, protein, or other materials to perform a particular activity defined herein.

"Operably linked" as used herein refers to a functional relationship between two or more nucleic acid (e.g., DNA) segments. Typically, it refers to the functional relationship of transcriptional regulatory element to a transcribed sequence. For example, a promoter is operably linked to a coding sequence, such as a polynucleotide defined herein, if it stimulates or modulates the transcription of the coding sequence in an appropriate host cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

The term "signal peptide" refers to an amino terminal polypeptide preceding a secreted mature protein. The signal peptide is cleaved from and is therefore not present in the mature protein. Signal peptides have the function of directing and trans-locating secreted proteins across cell membranes. The signal peptide is also referred to as signal sequence.

As used herein, "transformation" is the acquisition of new genes in a cell by the incorporation of a polynucleotide.

As used herein, the term "drug" refers to any compound that can be used to treat or prevent a particular disease, examples of drugs which can be formulated with a silk protein of the invention include, but are not limited to, proteins, nucleic acids, anti-tumor agents, analgesics, antibiotics, anti-inflammatory compounds (both steroidal and non-steroidal), hormones, vaccines, labeled substances, and the like.

Polypeptides

By "substantially purified polypeptide" or "purified polypeptide" we mean a polypeptide that has generally been separated from the lipids, nucleic acids, other polypeptides, and other contaminating molecules such as wax with which it is associated in its native state. With the exception of other proteins of the invention, it is preferred that the substantially purified polypeptide is at least 60% free, more preferably at least 75% free, and more preferably at least 90% free from other components with which it is naturally associated. In one aspect, the present invention relates to a homogenous population of, or composition comprising, a single type of collagen-like silk protein of the invention which does not exist in nature.

The term "recombinant" in the context of a polypeptide refers to the polypeptide when produced by a cell, or in a cell-free expression system, in an altered amount or at an altered rate compared to its native state. In one embodiment the cell is a cell that does not naturally produce the polypeptide. However, the cell may be a cell which comprises a non-endogenous gene that causes an altered, preferably increased, amount of the polypeptide to be produced. A recombinant polypeptide of the invention includes polypeptides which have not been separated from other components of the transgenic (recombinant) cell, or cell-free expression system, in which it is produced, and polypeptides produced in such cells or cell-free systems which are subsequently purified away from at least some other components.

The terms "polypeptide" and "protein" are generally used interchangeably and refer to a single polypeptide chain which may or may not be modified by addition of non-amino acid groups. In an embodiment, the terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

As used herein a "biologically active" fragment is a portion of a polypeptide of the invention which maintains a defined activity of the full-length polypeptide, namely the ability to be used to produce silk. Biologically active fragments can be any size as long as they maintain the defined activity. Preferably, biologically active fragments are, where relevant, at least 100, more preferably at least 200, and even more preferably at least 225 amino acids in length. In an embodiment, a "biologically active" fragment of the invention comprises a collagen-like domain of a polypeptide of the invention such as those provided in FIG. 1.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics.

Mutant (altered) polypeptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides of the invention are subjected to DNA shuffling techniques as broadly described by Harayama (1998). These DNA shuffling techniques may include genes of the invention possibly in addition to genes related to those of the present invention, such as silk genes from Hymenopteran species other than the specific species characterized herein. Products derived from mutated/altered DNA can readily be screened using techniques described herein to determine if they can be used as silk proteins.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to about 150 residues.

Substitution mutants have at least one amino acid residue in the polypeptide molecule removed and a different residue inserted in its place. The sites of greatest interest for substitutional mutagenesis include sites identified as important for function. Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

TABLE 1

| Exemplary substitutions | |
|---|---|
| Original Residue | Exemplary Substitutions |
| Ala (A) | val; leu; ile; ser; thr |
| Arg (R) | lys |
| Asn (N) | gln; his |
| Asp (D) | glu |
| Cys (C) | ser; thr; ala; gly; val |
| Gln (Q) | asn; his |
| Glu (E) | asp |
| Gly (G) | pro; ala; ser; val; thr |
| His (H) | asn; gln |
| Ile (I) | leu; val; ala; met |
| Leu (L) | ile; val; met; ala; phe |
| Lys (K) | arg |
| Met (M) | leu; phe |
| Phe (F) | leu; val; ala |
| Pro (P) | ala; ser; thr |
| Ser (S) | thr; ala; val; gln |
| Thr (T) | ser; gln; ala |
| Trp (W) | tyr |
| Tyr (Y) | trp; phe |
| Val (V) | ile; leu; met; phe; ala; ser; thr |

In a particularly preferred embodiment, unlike collagen, a collagen-like silk protein of the invention does not have any hydroxyproline.

Preferably, collagen-like silk proteins of the invention comprise at least about 40, more preferably at least about 50, Gly-X-Y triplets, where X and Y can be any amino acid. In a further embodiment, collagen-like silk proteins of the invention comprise between about 40 and about 150, more preferably between about 50 and about 100, Gly-X-Y triplets.

In a further preferred embodiment, the Gly-X-Y triplets constitute at least about 40%, more preferably at least about 50%, of the primary amino acid sequence of the proteins.

Further guidance regarding amino acid substitutions, particularly in the collagen-like domain, can be found in Persikov et al. (2005).

In an embodiment, it is preferred that a substitution in the Y position is not with an amino acid with a branched β-carbon.

In an embodiment, the polypeptides provided as SEQ ID NO's 2, 4 and 6 comprise an N-terminal methionine.

In an embodiment, a collagen-like silk polypeptide of the invention has, or is capable of forming under suitable conditions, a triple helical structure. Folding of the silk proteins into a triple helical structure may be enhanced by addition (for example production as a fusion protein) of a triple helix promoting sequence, for example the Scl2 V-domain from *S. pyogenes*. Other examples include, but are not limited to, foldon or trimeric coiled-coil sequences.

In another embodiment, a polypeptide (and/or fusion protein) of the invention comprises multimers of the collagen-like domain, or a fragment thereof capable of forming a triple helical structure (examples of such domains are provided in FIG. 1). The multimer may comprise collagen-like domains, or fragments thereof, from numerous different polypeptides of the invention, or comprise identical repeats of the same domain or a fragment thereof. The number of repeats may be, for example, 4 to 15, or 5 to 12.

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-aminohexanoic acid, 2-aminoisobutyric acid, 3-aminopropionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methylamino acids, Ca-methyl amino acids, Na-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

Polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and Petri plates. Culturing can be carried out at a temperature, pH and oxygen content appropriate for a recombinant cell. Such culturing conditions are within the expertise of one of ordinary skill in the art.

Polynucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. Furthermore, the term "polynucleotide" is used interchangeably herein with the term "nucleic acid".

The term "exogenous" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components.

The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

With regard to the defined polynucleotides, it will be appreciated that % identity figures higher than those provided above will encompass preferred embodiments. Thus, where applicable, in light of the minimum % identity figures, it is preferred that a polynucleotide of the invention comprises a sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

Oligonucleotides and/or polynucleotides of the invention hybridize to a silk gene of the present invention, or a region flanking said gene, under stringent conditions. The term "stringent hybridization conditions" and the like as used herein refers to parameters with which the art is familiar, including the variation of the hybridization temperature with length of an oligonucleotide. Nucleic acid hybridization parameters may be found in references which compile such methods, Sambrook, et al. (supra), and Ausubel, et al. (supra). For example, stringent hybridization conditions, as used herein, can refer to hybridization at 65° C. in hybridization buffer (3.5×SSC, 0.02% Ficoll, 0.02% polyvinyl pyrrolidone, 0.02% Bovine Serum Albumin (BSA), 2.5 mM $NaH_2PO_4$ (pH7), 0.5% SDS, 2 mM EDTA), followed by one or more washes in 0.2×SSC, 0.01% BSA at 50° C. Alternatively, the nucleic acid and/or oligonucleotides (which may also be referred to as "primers" or "probes") hybridize to the region of the an insect genome of interest, such as the genome of a *Nematus* sp., under conditions used in nucleic acid amplification techniques such as PCR.

Oligonucleotides of the present invention can be RNA, DNA, or derivatives of either. Although the terms polynucleotide and oligonucleotide have overlapping meaning, oligonucleotides are typically relatively short single stranded molecules. The minimum size of such oligonucleotides is the size required for the formation of a stable hybrid between an oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length.

Usually, monomers of a polynucleotide or oligonucleotide are linked by phosphodiester bonds or analogs thereof to form oligonucleotides ranging in size from relatively short monomeric units, e.g., 12-18, to several hundreds of monomeric units. Analogs of phosphodiester linkages include: phosphorothioate, phosphorodithioate, phosphoroselenoate, phosphorodiselenoate, phosphoroanilothioate, phosphoranilidate, phosphoramidate.

The present invention includes oligonucleotides that can be used as, for example, probes to identify nucleic acid molecules, or primers to produce nucleic acid molecules. Oligonucleotides of the present invention used as a probe are typically conjugated with a detectable label such as a radioisotope, an enzyme, biotin, a fluorescent molecule or a chemiluminescent molecule.

Recombinant Vectors

One embodiment of the present invention includes a recombinant vector, which comprises at least one isolated polynucleotide molecule of the present invention, inserted into any vector capable of delivering the polynucleotide molecule into a host cell. Such a vector contains heterologous polynucleotide sequences, which are polynucleotide sequences that are not naturally found adjacent to polynucleotide molecules of the present invention and that preferably are derived from a species other than the species from which the polynucleotide molecule(s) are derived. The vector can be either RNA or DNA, either prokaryotic or eukaryotic, and typically is a transposon (such as described in U.S. Pat. No. 5,792,294), a virus or a plasmid.

One type of recombinant vector comprises a polynucleotide molecule of the present invention operatively linked to an expression vector. The phrase operatively linked refers to insertion of a polynucleotide molecule into an expression vector in a manner such that the molecule is able to be expressed when transformed into a host cell. As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, animal, and plant cells. Particularly preferred expression vectors of the present invention can direct gene expression in plants cells. Vectors of the invention can also be used to produce the polypeptide in a cell-free expression system, such systems are well known in the art.

In particular, expression vectors of the present invention contain regulatory sequences such as transcription control sequences, translation control sequences, origins of replication, and other regulatory sequences that are compatible with the recombinant cell and that control the expression of polynucleotide molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, arthropod, plant or mammalian cells, such as, but not limited to, tac, lac, trp, trc, oxy-pro, omp/lpp, rrnB, bacteriophage lambda, bacteriophage T7, T7lac, bacteriophage T3, bacteriophage SP6, bacteriophage SP01, metallothionein, alpha-mating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells.

Examples of useful expression vectors include, but are not limited to, pColdI, pColdII, pColdIII and pColdIV (pCold Vector Information: catalog.takara-bio.co.jp/en/product/basic_info.asp?unitid=U1000058-56).

Particularly preferred transcription control sequences are promoters active in directing transcription in plants, either constitutively or stage and/or tissue specific, depending on the use of the plant or parts thereof. These plant promoters include, but are not limited to, promoters showing constitutive expression, such as the 35S promoter of Cauliflower Mosaic Virus (CaMV), those for leaf-specific expression, such as the promoter of the ribulose bisphosphate carboxylase small subunit gene, those for root-specific expression, such as the promoter from the glutamine synthase gene, those for seed-specific expression, such as the cruciferin A promoter from *Brassica napus*, those for tuber-specific expression, such as the class-I patatin promoter from potato or those for fruit-specific expression, such as the polygalacturonase (PG) promoter from tomato.

Recombinant molecules of the present invention may also (a) contain secretory signals (i.e., signal segment nucleic acid sequences) to enable an expressed polypeptide of the present invention to be secreted from the cell that produces the polypeptide and/or (b) contain fusion sequences which lead to the expression of nucleic acid molecules of the present invention as fusion proteins. Examples of suitable signal segments include any signal segment capable of directing the secretion of a polypeptide of the present invention. Preferred signal segments include, but are not limited to, tissue plasminogen activator (t-PA), interferon, interleukin, growth hormone, viral envelope glycoprotein signal segments, *Nicotiana nectarin* signal peptide (U.S. Pat. No. 5,939,288), tobacco extensin signal, the soy oleosin oil body binding protein signal, *Arabidopsis thaliana* vacuolar basic chitinase signal peptide, as well as native signal sequences of a polypeptide of the invention. In addition, a nucleic acid molecule of the present invention can be joined to a fusion segment that directs the encoded polypeptide to the proteosome, such as an ubiquitin fusion segment. Recombinant molecules may also include intervening and/or untranslated sequences surrounding and/or within the nucleic acid sequences of the present invention.

Host Cells

Another embodiment of the present invention includes a recombinant cell comprising a host cell transformed with one or more recombinant molecules of the present invention, or progeny cells thereof. Transformation of a polynucleotide molecule into a cell can be accomplished by any method by which a polynucleotide molecule can be inserted into the cell.

Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotide molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide of the present invention. Host cells of the present invention either can be endogenously (i.e., naturally) capable of producing polypeptides of the present invention or can be capable of producing such polypeptides after being transformed with at least one polynucleotide molecule of the present invention. Host cells of the present invention can be any cell capable of producing at least one protein of the present invention, and include bacterial, fungal (including yeast), parasite, arthropod, animal and plant cells. Examples of host cells include *Salmonella, Escherichia, Bacillus, Listeria, Saccharomyces, Spodoptera, Mycobacteria, Trichoplusia*, BHK (baby hamster kidney) cells, MDCK cells, CRFK cells, CV-1 cells, COS (e.g., COS-7) cells, and Vero cells. Further examples of host cells are *E. coli*, including *E. coli* K-12 derivatives; *Salmonella typhi; Salmonella typhimurium*, including attenuated strains; *Spodoptera frugiperda; Trichoplusia ni*; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK cells and/or HeLa cells. Particularly preferred host cells are plant cells such as those available from Deutsche Sammlung von Mikroorganismen and Zellkulturen GmbH (German Collection of Microorganisms and Cell Cultures).

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules of the present invention include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules of the present invention to correspond to the codon usage of the host cell, and the deletion of sequences that destabilize transcripts.

Transgenic Plants

The term "plant" refers to whole plants, plant organs (e.g. leaves, stems, roots etc), seeds, plant cells and the like. Plants contemplated for use in the practice of the present invention include both monocotyledons and dicotyledons. Target plants include, but are not limited to, the following: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers).

Transgenic plants, as defined in the context of the present invention, include plants (as well as parts and cells of said plants) and their progeny which have been genetically modified using recombinant techniques to cause production of at least one polypeptide of the present invention in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

A polynucleotide of the present invention may be expressed constitutively in the transgenic plants during all stages of development. Depending on the use of the plant or plant organs, the polypeptides may be expressed in a stage-specific manner. Furthermore, the polynucleotides may be expressed tissue-specifically.

Regulatory sequences which are known or are found to cause expression of a gene encoding a polypeptide of interest in plants may be used in the present invention. The choice of the regulatory sequences used depends on the target plant and/or target organ of interest. Such regulatory sequences may be obtained from plants or plant viruses, or may be chemically synthesized. Such regulatory sequences are well known to those skilled in the art.

Constitutive plant promoters are well known. Further to previously mentioned promoters, some other suitable promoters include but are not limited to the nopaline synthase promoter, the octopine synthase promoter, CaMV 35S promoter, the ribulose-1,5-bisphosphate carboxylase promoter, Adh1-based pEmu, Act1, the SAM synthase promoter and Ubi promoters and the promoter of the chlorophyll a/b binding protein. Alternatively it may be desired to have the transgene(s) expressed in a regulated fashion. Regulated expression of the polypeptides is possible by placing the coding sequence of the silk protein under the control of promoters that are tissue-specific, developmental-specific, or inducible. Several tissue-specific regulated genes and/or promoters have been reported in plants. These include genes encoding the seed storage proteins (such as napin, cruciferin, β-conglycinin, glycinin and phaseolin), zein or oil body proteins (such as oleosin), or genes involved in fatty acid biosynthesis (including acyl carrier protein, stearoyl-ACP desaturase, and fatty acid desaturases (FAD 2-1)), and other genes expressed during embryo development (such as Bce4). Particularly useful for seed-specific expression is the pea vicilin promoter. Other useful promoters for expression in mature leaves are those that are switched on at the onset of senescence, such as the SAG promoter from *Arabidopsis*). A class of fruit-specific promoters expressed at or during anthesis through fruit development, at least until the beginning of ripening, is discussed in U.S. Pat. No. 4,943,674. Other examples of tissue-specific promoters include those that direct expression in tubers (for example, patatin gene promoter), and in fibre cells (an example of a developmentally-regulated fibre cell protein is E6 fibre).

Other regulatory sequences such as terminator sequences and polyadenylation signals include any such sequence functioning as such in plants, the choice of which would be obvious to the skilled addressee. The termination region used in the expression cassette will be chosen primarily for convenience, since the termination regions appear to be relatively interchangeable. The termination region which is used may be native with the transcriptional initiation region, may be native with the polynucleotide sequence of interest, or may be derived from another source. The termination region may be naturally occurring, or wholly or partially synthetic. Convenient termination regions are available from the Ti-plasmid of *A. tumefaciens*, such as the octopine synthase and nopaline synthase termination regions or from the genes for β-phaseolin, the chemically inducible plant gene, pIN.

Several techniques are available for the introduction of an expression construct containing a nucleic acid sequence encoding a polypeptide of interest into the target plants. Such techniques include but are not limited to transformation of protoplasts using the calcium/polyethylene glycol method, electroporation and microinjection or (coated) particle bombardment. In addition to these so-called direct DNA transformation methods, transformation systems involving vectors are widely available, such as viral and bacterial vectors (e.g. from the genus *Agrobacterium*). After selection and/or screening, the protoplasts, cells or plant parts that have been transformed can be regenerated into whole plants, using methods known in the art. The choice of the transformation and/or regeneration techniques is not critical for this invention.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts may be harvested, and/or the seed collected. The seed may serve as a source for growing additional plants with tissues or parts having the desired characteristics.

Transgenic Non-Human Animals

Techniques for producing transgenic animals are well known in the art. A useful general textbook on this subject is Houdebine, Transgenic animals—Generation and Use (Harwood Academic, 1997).

Heterologous DNA can be introduced, for example, into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a highly preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos are allowed to develop into mature transgenic animals.

Another method used to produce a transgenic animal involves microinjecting a nucleic acid into pro-nuclear stage eggs by standard methods. Injected eggs are then cultured before transfer into the oviducts of pseudopregnant recipients.

Transgenic animals may also be produced by nuclear transfer technology. Using this method, fibroblasts from donor animals are stably transfected with a plasmid incorporating the coding sequences for a binding domain or binding partner of interest under the control of regulatory sequences. Stable transfectants are then fused to enucleated oocytes, cultured and transferred into female recipients.

In one embodiment, the transgenic non-human animal is *Bombyx* silkworms (Tomita et al., 2011).

Recovery Methods and Production of Silk

The silk proteins of the present invention may be extracted and purified from recombinant cells, such as plant, animal, bacteria or yeast cells, producing said protein by a variety of methods. In one embodiment, the method involves removal of proteins from homogenized cells/tissues/plants etc by lowering pH and heating (to no more than 4° C., preferably no more than 10° C., below the melting temperature of the triple helix), followed by ammonium sulfate fractionation. Briefly, total soluble proteins are extracted by homogenizing cells/tissues/plants. Proteins are removed by precipitation at pH 4.7 and then at 60° C. The resulting supernatant is then fractionated with ammonium sulfate at 40% saturation. The resulting protein will be of the order of 95% pure. Additional purification may be achieved with conventional gel or affinity chromatography.

In another example, cell lysates are treated with high concentrations of acid e.g. HCl or propionic acid to reduce pH to ~1-2 for 1 hour or more which will solubilise the silk proteins but precipitate other proteins.

Fibrillar aggregates will form from solutions by spontaneous self-assembly of silk proteins of the invention when the protein concentration exceeds a critical value with selected pH and ionic strength conditions. The aggregates may be gathered and mechanically spun into macroscopic fibres according to the method of O'Brien et al. ("Design, Synthesis and Fabrication of Novel Self-Assembling Fibrillar Proteins", in Silk Polymers: Materials Science and Biotechnology, pp. 104-117, Kaplan, Adams, Farmer and Viney, eds., (1994) by American Chemical Society, Washington, D.C.).

Products of the invention have a low processing requirement. The silk proteins of the invention require minimal processing, e.g. spinning, to form a strong fibre. This contrasts with *B. mori* and spider recombinant silk polypeptides which require sophisticated spinning techniques in order to obtain the secondary structure (n-sheet) and strength of the fibre.

However, fibres may be spun from solutions having properties characteristic of a liquid crystal phase. The fibre concentration at which phase transition can occur is dependent on the composition of a protein or combination of proteins present in the solution. Phase transition, however, can be detected by monitoring the clarity and birefringence of the solution. Onset of a liquid crystal phase can be detected when the solution acquires a translucent appearance and registers birefringence when viewed through crossed polarizing filters.

In one fibre-forming technique, fibres can first be extruded from the protein solution through an orifice into methanol, until a length sufficient to be picked up by a mechanical means is produced. Then a fibre can be pulled by such mechanical means through a methanol solution, collected, and dried. Methods for drawing fibres are considered well-known in the art.

In one embodiment, extrusion into precipitants such as ammonium sulphate of polyethylene glycol is used.

Further examples of methods which may be used for producing products of the present are described in US 2004/0170827 and US 2005/0054830.

In a preferred embodiment, silk proteins of the invention, such as when in the form of a tube, rod or sponge, are crosslinked. In one embodiment, the proteins are crosslinked to a surface/article/product etc of interest using techniques known in the art. In another embodiment (or in combination with the previous embodiment), at least some silk proteins are crosslinked to each other. Such crosslinking can be performed using chemical and/or enzymatic techniques known in the art. For example, enzymatic cross-links can be catalysed by lysyl oxidase, whereas nonenzymatic cross-links can be generated from glycated lysine residues (Reiser et al., 1992) or using transglutaminase. In another embodiment, the silk proteins of the invention are cross-linked by glutaraldehydes. With the preponderance of Tyr residues particularly in the B and C chains, photochemical cross-linking which involves just this residue could be useful (Elvin et al., 2010). See Ramshaw et al. (2000) Stabilisation of collagen in clinical applications. In: Handbook of Biomaterials Engineering, Wise, D. L. (Ed.), Marcel Dekker Inc., New York, pp. 717-738, for further details of cross-linking.

Antibodies

The term "antibody" as used in this invention includes polyclonal antibodies, monoclonal antibodies, bispecific antibodies, diabodies, triabodies, heteroconjugate antibodies, chimeric antibodies including intact molecules as well as fragments thereof, such as Fab, F(ab')2, and Fv which are capable of binding the epitopic determinant, and other antibody-like molecules.

Antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab)2 is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, Antibodies: A Laboratory Manual, Cold Spring Harbor Laboratory, New York (1988)).

(6) Single domain antibody, typically a variable heavy domain devoid of a light chain.

The phrase "specifically binds" means that under particular conditions, the compound binds a polypeptide of the invention and does not bind to a significant amount to other, for example, proteins or carbohydrates. Specific binding may require an antibody that is selected for its specificity. In another embodiment, an antibody is considered to "specifically binds" if there is a greater than 10 fold difference, and preferably a 25, 50 or 100 fold greater difference between the binding of the antibody to a polypeptide of the invention when compared to another protein, especially a silk protein or a collagen protein (for example from mammals).

As used herein, the term "epitope" refers to a region of a polypeptide of the invention which is bound by the antibody. An epitope can be administered to an animal to generate antibodies against the epitope, however, antibodies of the present invention preferably specifically bind the epitope region in the context of the entire polypeptide.

If polyclonal antibodies are desired, a selected mammal (e.g., mouse, rabbit, goat, horse, etc) is immunised with an immunogenic polypeptide of the invention. Serum from the immunised animal is collected and treated according to known procedures. If serum containing polyclonal antibodies contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals.

Monoclonal antibodies directed against polypeptides of the invention can also be readily produced by one skilled in the art. The general methodology for making monoclonal antibodies by hybridomas is well known Immortal antibody-producing cell lines can be created by cell fusion, and also by other techniques such as direct transformation of B lymphocytes with oncogenic DNA, or transfection with Epstein-Barr virus. Panels of monoclonal antibodies produced can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

Other techniques for producing antibodies of the invention are known in the art.

Antibodies of the invention may be bound to a solid support and/or packaged into kits in a suitable container along with suitable reagents, controls, instructions and the like.

In an embodiment, antibodies of the present invention are detectably labeled. Exemplary detectable labels that allow for direct measurement of antibody binding include radiolabels, fluorophores, dyes, magnetic beads, chemiluminescers, colloidal particles, and the like. Examples of labels which permit indirect measurement of binding include enzymes where the substrate may provide for a coloured or fluorescent product. Additional exemplary detectable labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Further, exemplary detectable labels include biotin, which binds with high affinity to avidin or streptavidin; fluorochromes (e.g., phycobiliproteins, phycoerythrin and allophycocyanins; fluorescein and Texas red), which can be used with a fluorescence activated cell sorter; haptens; and the like. Preferably, the detectable label allows for direct measurement in a plate luminometer, for example, biotin. Such labeled antibodies can be used in techniques known in the art to detect polypeptides of the invention.

Compositions

Compositions of the present invention may include an "acceptable carrier". Examples of such acceptable carriers include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used.

In one embodiment, the "acceptable carrier" is a "pharmaceutically acceptable carrier". The term pharmaceutically acceptable carrier refers to molecular entities and compositions that do not produce an allergic, toxic or otherwise adverse reaction when administered to an animal, particularly a mammal, and more particularly a human. Useful examples of pharmaceutically acceptable carriers or diluents include, but are not limited to, solvents, dispersion media, coatings, stabilizers, protective colloids, adhesives, thickeners, thixotropic agents, penetration agents, sequestering agents and isotonic and absorption delaying agents that do not affect the activity of the polypeptides of the invention. The proper fluidity can be maintained, for example, by the use of a coating, such as lecithin, by the maintenance of the required particle size in the case of dispersion and by the use of surfactants. More generally, the polypeptides of the invention can be combined with any non-toxic solid or liquid additive corresponding to the usual formulating techniques.

As outlined herein, in some embodiments a product comprising silk proteins of the invention is used as a pharmaceutically acceptable carrier.

Other suitable compositions are described below with specific reference to specific uses of the polypeptides of the invention.

Uses

Silk proteins are useful for the creation of new biomaterials because of their exceptional toughness and strength. However, the fibrous proteins of spiders and insects are generally large proteins (over 100 kDa) and consist of highly repetitive amino acid sequences. These proteins are encoded by large genes containing highly biased codons making them particularly difficult to produce in recombinant systems. By comparison, the silk proteins of the invention are short and less-repetitive. These properties make the genes encoding these proteins particularly attractive for recombinant production of new biomaterials.

The silk proteins of the invention can be used for a broad and diverse array of medical, military, industrial and commercial applications. Silk proteins, for example in the form of silk fibres, can be used in the manufacture of medical devices such as sutures, skin grafts, cellular growth matrices, replacement ligaments, and surgical mesh, and in a wide range of industrial and commercial products, such as, for example, cable, rope, netting, fishing line, clothing fabric, bullet-proof vest lining, container fabric, backpacks, knapsacks, bag or purse straps, adhesive binding material, non-adhesive binding material, strapping material, tent fabric, tarpaulins, pool covers, vehicle covers, fencing material, sealant, construction material, weatherproofing material, flexible partition material, sports equipment; and, in fact, in nearly any use of fibre or fabric for which high tensile strength and elasticity are desired characteristics. The silk proteins, for example in the form of silk fibres, and/or copolymers of the present invention also have applications in compositions for personal care products such as cosmetics, skin care, hair care and hair colouring; and in coating of particles, such as pigments.

The silk proteins may be used in their native form or they may be modified to form derivatives, which provide a more beneficial effect. For example, the silk protein may be modified by conjugation to a polymer to reduce allergenicity as described in U.S. Pat. No. 5,981,718 and U.S. Pat. No. 5,856,451. Suitable modifying polymers include, but are not limited to, polyalkylene oxides, polyvinyl alcohol, polycarboxylates, polyvinylpyrolidone, and dextrans. In another example, the silk proteins may be modified by selective digestion and splicing of other protein modifiers. For example, the silk proteins may be cleaved into smaller peptide units by treatment with acid at an elevated temperature of about 60° C. The useful acids include, but are not limited to, dilute hydrochloric, sulfuric or phosphoric acids. Alternatively, digestion of the silk proteins may be done by treatment with a base, such as sodium hydroxide, or enzymatic digestion using a suitable protease may be used.

The proteins may be further modified to provide performance characteristics that are beneficial in specific applications for personal care products. The modification of proteins for use in personal care products is well known in the art. For example, commonly used methods are described in U.S. Pat. No. 6,303,752, U.S. Pat. No. 6,284,246, and U.S. Pat. No. 6,358,501. Examples of modifications include, but are not limited to, ethoxylation to promote water-oil emulsion enhancement, siloxylation to provide lipophilic compatibility, and esterification to aid in compatibility with soap and detergent compositions. Additionally, the silk proteins may be derivatized with functional groups including, but not limited to, amines, oxiranes, cyanates, carboxylic acid esters, silicone copolyols, siloxane esters, quaternized amine aliphatics, urethanes, polyacrylamides, dicarboxylic acid esters, and halogenated esters. The silk proteins may also be derivatized by reaction with diimines and by the formation of metal salts.

Consistent with the above definitions of "polypeptide" (and "protein"), such derivatized and/or modified molecules are also referred to herein broadly as "polypeptides" and "proteins".

Silk proteins of the invention can be spun together and/or bundled or braided with other fibre types. Examples include, but are not limited to, polymeric fibres (e.g., polypropylene, nylon, polyester), fibres and silks of other plant and animal sources (e.g., cotton, wool, Bombyx mori, spider silk or honey bee (for example see, WO 2007/038837), and glass fibres. A preferred embodiment is silk fibre braided with 10% polypropylene fibre. The present invention contemplates that the production of such combinations of fibres can be readily practiced to enhance any desired characteristics, e.g., appearance, softness, weight, durability, water-repellant properties, improved cost-of-manufacture, that may be generally sought in the manufacture and production of silk protein comprising products, for example fibres, for medical, industrial, or commercial applications.

Silk proteins of the invention can be used to stabilize compounds, for example therapeutic drugs such as vaccines and antibioctics, during shipping and/or storage (see, for example, Zhang et al., 2012).

Personal Care Products

Cosmetic and skin care compositions may be anhydrous compositions comprising an effective amount of silk protein in a cosmetically acceptable medium. The uses of these compositions include, but are not limited to, skin care, skin cleansing, make-up, and anti-wrinkle products. An effective amount of a silk protein for cosmetic and skin care compositions is herein defined as a proportion of from about $10^{-4}$ to about 30% by weight, but preferably from about $10^{-3}$ to 15% by weight, relative to the total weight of the composition. This proportion may vary as a function of the type of cosmetic or skin care composition. Suitable compositions for a cosmetically acceptable medium are described in U.S. Pat. No. 6,280,747. For example, the cosmetically acceptable medium may contain a fatty substance in a proportion generally of from about 10 to about 90% by weight relative to the total weight of the composition, where the fatty phase containing at least one liquid, solid or semi-solid fatty substance. The fatty substance includes, but is not limited to, oils, waxes, gums, and so-called pasty fatty substances. Alternatively, the compositions may be in the form of a stable dispersion such as a water-in-oil or oil-in-water emulsion. Additionally, the compositions may contain one or more conventional cosmetic or dermatological additives or adjuvants, including but not limited to, antioxidants, preserving agents, fillers, surfactants, UVA and/or UVB sunscreens, fragrances, thickeners, wetting agents and anionic, nonionic or amphoteric polymers, and dyes or pigments.

Emulsified cosmetics and quasi drugs which are producible with the use of emulsified materials comprising at least one silk protein of the present invention include, for example, cleansing cosmetics (beauty soap, facial wash, shampoo, rinse, and the like), hair care products (hair dye, hair cosmetics, and the like), basic cosmetics (general cream, emulsion, shaving cream, conditioner, cologne, shaving lotion, cosmetic oil, facial mask, and the like), make-up cosmetics (foundation, eyebrow pencil, eye cream, eye shadow, mascara, and the like), aromatic cosmetics (perfume and the like), tanning and sunscreen cosmetics (tanning and sunscreen cream, tanning and sunscreen lotion, tanning and sunscreen oil, and the like), nail cosmetics (nail cream and the like), eyeliner cosmetics (eyeliner and the like), lip cosmetics (lipstick, lip cream, and the like), oral care products (tooth paste and the like) bath cosmetics (bath products and the like), and the like.

The cosmetic composition may also be in the form of products for nail care, such as a nail varnish. Nail varnishes are herein defined as compositions for the treatment and colouring of nails, comprising an effective amount of silk protein in a cosmetically acceptable medium. An effective amount of a silk protein for use in a nail varnish composition is herein defined as a proportion of from about $10^{-4}$ to about 30% by weight relative to the total weight of the varnish. Components of a cosmetically acceptable medium for nail varnishes are described in U.S. Pat. No. 6,280,747. The nail varnish typically contains a solvent and a film forming substance, such as cellulose derivatives, polyvinyl derivatives, acrylic polymers or copolymers, vinyl copolymers and polyester polymers. The composition may also contain an organic or inorganic pigment.

Hair care compositions are herein defined as compositions for the treatment of hair, including but not limited to shampoos, conditioners, lotions, aerosols, gels, and mousses, comprising an effective amount of silk protein in a cosmetically acceptable medium. An effective amount of a silk protein for use in a hair care composition is herein defined as a proportion of from about $10^{-2}$ to about 90% by weight relative to the total weight of the composition. Components of a cosmetically acceptable medium for hair care compositions are described in US 2004/0170590, U.S. Pat. No. 6,280,747, U.S. Pat. No. 6,139,851, and U.S. Pat. No. 6,013,250. For example, these hair care compositions can be aqueous, alcoholic or aqueous-alcoholic solutions, the alcohol preferably being ethanol or isopropanol, in a proportion of from about 1 to about 75% by weight relative to the total weight, for the aqueous-alcoholic solutions. Additionally, the hair care compositions may contain one or more conventional cosmetic or dermatological additives or adjuvants, as given above.

Hair colouring compositions are herein defined as compositions for the colouring, dyeing, or bleaching of hair, comprising an effective amount of silk protein in a cosmetically acceptable medium. An effective amount of a silk protein for use in a hair colouring composition is herein defined as a proportion of from about $10^{-4}$ to about 60% by weight relative to the total weight of the composition. Components of a cosmetically acceptable medium for hair colouring compositions are described in US 2004/0170590, U.S. Pat. No. 6,398,821 and U.S. Pat. No. 6,129,770. For example, hair colouring compositions generally contain a mixture of inorganic peroxygen-based dye oxidizing agent and an oxidizable coloring agent. The peroxygen-based dye oxidizing agent is most commonly hydrogen peroxide. The oxidative hair coloring agents are formed by oxidative coupling of primary intermediates (for example p-phenylenediamines, p-aminophenols, p-diaminopyridines, hydroxyindoles, aminoindoles, aminothymidines, or cyanophenols) with secondary intermediates (for example phenols, resorcinols, m-aminophenols, m-phenylenediamines, naphthols, pyrazolones, hydroxyindoles, catechols or pyrazoles). Additionally, hair colouring compositions may contain oxidizing acids, sequestrants, stabilizers, thickeners, buffers carriers, surfactants, solvents, antioxidants, polymers, non-oxidative dyes and conditioners.

The silk proteins can also be used to coat pigments and cosmetic particles in order to improve dispersibility of the particles for use in cosmetics and coating compositions. Cosmetic particles are herein defined as particulate materials such as pigments or inert particles that are used in cosmetic compositions. Suitable pigments and cosmetic particles include, but are not limited to, inorganic color pigments, organic pigments, and inert particles. The inorganic color pigments include, but are not limited to, titanium dioxide, zinc oxide, and oxides of iron, magnesium, cobalt, and aluminium. Organic pigments include, but are not limited to, D&C Red No. 36, D&C Orange No. 17, the calcium lakes of D&C Red Nos. 7, 11, 31 and 34, the barium lake of D&C Red No. 12, the strontium lake D&C Red No. 13, the aluminium lake of FD&C Yellow No. 5 and carbon black particles. Inert particles include, but are not limited to, calcium carbonate, aluminium silicate, calcium silicate, magnesium silicate, mica, talc, barium sulfate, calcium sulfate, powdered Nylon™, perfluorinated alkanes, and other inert plastics.

The silk proteins may also be used in dental floss (see, for example, US 2005/0161058). The floss may be monofilament yarn or multifilament yarn, and the fibres may or may not be twisted. The dental floss may be packaged as individual pieces or in a roll with a cutter for cutting pieces to any desired length. The dental floss may be provided in a variety of shapes other than filaments, such as but not limited to, strips and sheets and the like. The floss may be coated with different materials, such as but not limited to, wax, polytetrafluoroethylene monofilament yarn for floss.

The silk proteins may also be used in soap (see, for example, US 2005/0130857).

Pigment and Cosmetic Particle Coating

The effective amount of a silk protein for use in pigment and cosmetic particle coating is herein defined as a proportion of from about $10^{-4}$ to about 50%, but preferably from about 0.25 to about 15% by weight relative to the dry weight of particle. The optimum amount of the silk protein to be used depends on the type of pigment or cosmetic particle being coated. For example, the amount of silk protein used with inorganic color pigments is preferably between about 0.01% and 20% by weight. In the case of organic pigments, the preferred amount of silk protein is between about 1% to about 15% by weight, while for inert particles, the preferred amount is between about 0.25% to about 3% by weight. Methods for the preparation of coated pigments and particles are described in U.S. Pat. No. 5,643,672. These methods include: adding an aqueous solution of the silk protein to the particles while tumbling or mixing, forming a slurry of the silk protein and the particles and drying, spray drying a solution of the silk protein onto the particles or lyophilizing a slurry of the silk protein and the particles. These coated pigments and cosmetic particles may be used in cosmetic formulations, paints, inks and the like.

Biomedical

The silk proteins may be used as a coating on a bandage to promote wound healing. For this application, the bandage material is coated with an effective amount of the silk protein. For the purpose of a wound-healing bandage, an effective amount of silk protein is herein defined as a proportion of from about $10^{-4}$ to about 30% by weight relative to the weight of the bandage material. The material to be coated may be any soft, biologically inert, porous cloth or fibre. Examples include, but are not limited to, cotton, silk, rayon, acetate, acrylic, polyethylene, polyester, and combinations thereof. The coating of the cloth or fibre may be accomplished by a number of methods known in the art. For example, the material to be coated may be dipped into an aqueous solution containing the silk protein. Alternatively, the solution containing the silk protein may be sprayed onto the surface of the material to be coated using a spray gun. Additionally, the solution containing the silk protein may be coated onto the surface using a roller coat printing process. The wound bandage may include other additives including, but not limited to, disinfectants such as iodine, potassium iodide, povidon iodine, acrinol, hydrogen peroxide, benzalkonium chloride, and chlorohexidine; cure accelerating agents such as allantoin, dibucaine hydrochloride, and chlorophenylamine malate; vasoconstrictor agents such as naphazoline hydrochloride; astringent agents such as zinc oxide; and crust generating agents such as boric acid.

The silk proteins of the present invention may also be used in the form of a film as a wound dressing material. The use of silk proteins, in the form of an amorphous film, as a wound dressing material is described in U.S. Pat. No. 6,175,053. The amorphous film comprises a dense and nonporous film of a crystallinity below 10% which contains an effective amount of silk protein. For a film for wound care, an effective amount of silk protein is herein defined as between about 1 to 99% by weight. The film may also contain other components including but not limited to other proteins such as sericin, and disinfectants, cure accelerating agents, vasoconstrictor agents, astringent agents, and crust generating agents, as described above. Other proteins such as sericin may comprise 1 to 99% by weight of the composition. The amount of the other ingredients listed is preferably below a total of about 30% by weight, more preferably between about 0.5 to 20% by weight of the composition. The wound dressing film may be prepared by dissolving the above mentioned materials in an aqueous solution, removing insolubles by filtration or centrifugation, and casting the solution on a smooth solid surface such as an acrylic plate, followed by drying.

The silk proteins of the present invention may also be used in sutures (see, for example, US 2005/0055051). Such sutures can feature a braided jacket made of ultrahigh molecular weight fibres and silk fibres. The polyethylene provides strength. Polyester fibres may be woven with the high molecular weight polyethylene to provide improved tie down properties. The silk may be provided in a contrasting color to provide a trace for improved suture recognition and identification. Silk also is more tissue compliant than other fibres, allowing the ends to be cut close to the knot without concern for deleterious interaction between the ends of the suture and surrounding tissue. Handling properties of the high strength suture also can be enhanced using various materials to coat the suture. The suture advantageously has the strength of Ethibond No. 5 suture, yet has the diameter, feel and tieability of No. 2 suture. As a result, the suture is ideal for most orthopedic procedures such as rotator cuff repair, Achilles tendon repair, patellar tendon repair, ACL/PCL reconstruction, hip and shoulder reconstruction procedures, and replacement for suture used in or with suture anchors. The suture can be uncoated, or coated with wax (beeswax, petroleum wax, polyethylene wax, or others), silicone (Dow Corning silicone fluid 202A or others), silicone rubbers, PBA (polybutylate acid), ethyl cellulose (Filodel) or other coatings, to improve lubricity of the braid, knot security, or abrasion resistance, for example.

The silk proteins of the present invention may also be used in stents (see, for example, US 2004/0199241). For example, a stent graft is provided that includes an endoluminal stent and a graft, wherein the stent graft includes silk. The silk induces a response in a host who receives the stent graft, where the response can lead to enhanced adhesion between the silk stent graft and the host's tissue that is adjacent to the silk of the silk stent graft. The silk may be attached to the graft by any of various means, e.g., by interweaving the silk into the graft or by adhering the silk to the graft (e.g., by means of an adhesive or by means of suture). The silk may be in the form of a thread, a braid, a sheet, powder, etc. As for the location of the silk on the stent graft, the silk may be attached only the exterior of the stent, and/or the silk may be attached to distal regions of the stent graft, in order to assist in securing those distal regions to neighbouring tissue in the host. A wide variety of stent grafts may be utilized within the context of the present invention, depending on the site and nature of treatment desired. Stent grafts may be, for example, bifurcated or tube grafts, cylindrical or tapered, self-expandable or balloon-expandable, unibody or, modular, etc.

In addition to silk, the stent graft may contain a coating on some or all of the silk, where the coating degrades upon insertion of the stent graft into a host, the coating thereby delaying contact between the silk and the host. Suitable coatings include, without limitation, gelatin, degradable polyesters (e.g., PLGA, PLA, MePEG-PLGA, PLGA-PEG-PLGA, and copolymers and blends thereof), cellulose and cellulose derivatives (e.g., hydroxypropyl cellulose), polysaccharides (e.g., hyaluronic acid, dextran, dextran sulfate, chitosan), lipids, fatty acids, sugar esters, nucleic acid esters, polyanhydrides, polyorthoesters and polyvinylalcohol (PVA). The silk-containing stent grafts may contain a biologically active agent (drug), where the agent is released from the stent graft and then induces an enhanced cellular response (e.g., cellular or extracellular matrix deposition) and/or fibrotic response in a host into which the stent graft has been inserted.

The silk proteins of the present invention may also be used in a matrix for producing ligaments and tendons ex vivo (see, for example, US 2005/0089552). A silk-fibre-based matrix can be seeded with pluripotent cells, such as bone marrow stromal cells (BMSCs). The bioengineered ligament or tendon is advantageously characterized by a cellular orientation and/or matrix crimp pattern in the direction of applied mechanical forces, and also by the production of ligament and tendon specific markers including collagen type I, collagen type DI, and fibronectin proteins along the axis of mechanical load produced by the mechanical forces or stimulation, if such forces are applied. In a preferred embodiment, the ligament or tendon is characterized by the presence of fibre bundles which are arranged into a helical organization. Some examples of ligaments or tendons that can be produced include anterior cruciate ligament, posterior cruciate ligament, rotator cuff tendons, medial collateral ligament of the elbow and knee, flexor tendons of the hand, lateral ligaments of the ankle and tendons and ligaments of the jaw or temporomandibular joint. Other tissues that may be produced by methods of the present invention include cartilage (both articular and meniscal), bone, muscle, skin and blood vessels.

The silk proteins of the present invention may also be used in hydrogels (see, for example, US 2005/0266992). Silk fibroin hydrogels can be characterized by an open pore structure which allows their use as tissue engineering scaffolds, substrate for cell culture, wound and burn dressing, soft tissue substitutes, bone filler, and as well as support for pharmaceutical or biologically active compounds.

The silk proteins may also be used in dermatological compositions (see, for example, US 2005/0019297). Furthermore, the silk proteins of the invention and derivatives thereof may also be used in sustained release compositions (see, for example, US 2004/0005363 and US 2012/0195967).

Products comprising silk proteins of the invention may also more broadly be used as scaffolds for the culture (such as cell and/or tissue culture) and/or implantation of cells, such as stem cells (see, for example, US 2012/0189669, US 2012/0172985, US 2012/0171257, US 2011/0293685, US 20090214614, US 20110238179 and US 20070041952).

Textiles

The silk proteins of the present invention may also be applied to the surface of fibres for subsequent use in textiles. This provides a monolayer of the protein film on the fibre, resulting in a smooth finish. U.S. Pat. No. 6,416,558 and U.S. Pat. No. 5,232,611 describe the addition of a finishing coat to fibres. The methods described in these disclosures provide examples of the versatility of finishing the fibre to provide a good feel and a smooth surface. For this application, the fibre is coated with an effective amount of the silk protein. For the purpose of fibre coating for use in textiles, an effective amount of silk protein is herein defined as a proportion of from about 1 to about 99% by weight relative to the weight of the fibre material. The fibre materials include, but are not limited to textile fibres of cotton, polyesters such as rayon and Lycra™, nylon, wool, and other natural fibres including native silk. Compositions suitable for applying the silk protein onto the fibre may include co-solvents such as ethanol, isopropanol, hexafluoranols, isothiocyanouranates, and other polar solvents that can be mixed with water to form solutions or microemulsions. The silk protein-containing solution may be sprayed onto the fibre or the fibre may be dipped into the solution. While not necessary, flash drying of the coated material is preferred. An alternative protocol is to apply the silk protein composition onto woven fibres. An ideal embodiment of this application is the use of silk proteins to coat stretchable weaves such as used for stockings.

Composite Materials

Silk proteins, for example in the form of fibres, can be added to polyurethane, other resins or thermoplastic fillers to prepare panel boards and other construction material or as moulded furniture and benchtops that replace wood and particle board. The composites can be also be used in building and automotive construction, especially rooftops and door panels. The silk re-enforces the resin making the material much stronger and allowing lighterweight construction which is of equal or superior strength to other particle boards and composite materials. The silk proteins, for example in the form of fibres, may be isolated and added to a synthetic composite-forming resin or be used in combination with plant-derived proteins, starch and oils to produce a biologically-based composite materials. Processes for the production of such materials are described in JP 2004284246, US 2005175825, U.S. Pat. No. 4,515,737, JP 47020312 and WO 2005/017004.

Paper Additives

The fibre properties of the silk of the invention can add strength and quality texture to paper making. Silk papers are made by mottling silk threads in cotton pulp to prepare extra smooth handmade papers is used for gift wrapping, notebook covers, carry bags. Processes for production of paper products which can include silk proteins of the invention are generally described in JP 2000139755.

Advanced Materials

Silks of the invention have considerable toughness and stands out among other silks in maintaining these properties when wet (Hepburn et al., 1979).

Areas of substantial growth in the clothing textile industry are the technical and intelligent textiles. There is a rising demand for healthy, high value functional, environmentally friendly and personalized textile products. Fibres, such as those of the invention, that do not change properties when wet and in particular maintain their strength and extensibility are useful for functional clothing for sports and leisure wear as well as work wear and protective clothing.

Developments in the weapons and surveillance technologies are prompting innovations in individual protection equipments and battle-field related systems and structures. Besides conventional requirements such as material durability to prolonged exposure, heavy wear and protection from external environment, silk textiles of the invention can be processed to resist ballistic projectiles, fire and chemicals. Processes for the production of such materials are described in WO 2005/045122 and US 2005268443.

EXAMPLES

Example 1

Preparation and Analysis of Late Last Instar Salivary Gland cDNAs

The proteins that are found in sawfly (*Nematus oligospilus*, the willow sawfly) silks were identified from cDNAs isolated from the salivary gland of late final instar larvae. Willow sawfly larvae (*N. oligospilus* from the genus *Nematus*) were collected from *Salix* (willow) species around lake Burley Griffin in Canberra (Australia). Larvae were maintained on a diet of fresh willow leaves in the laboratory until required.

A *N. oligospilus* silk gland cDNA library was constructed after mRNA was isolated using the Micro-FastTrack™ 2.0 mRNA Isolation kit (Invitrogen) from 28.1 µg total RNA that had been isolated from the labial glands of 10 larval sawflies using the RNAqueous-4PCR kit (Ambion). The cDNA library was constructed from the mRNA using the Clone-Miner™ cDNA kit (Invitrogen). The cDNA library comprised approximately $2.9 \times 10^7$ colony forming units (cfu) with less than 1% of the original vector. The average insert size within the libraries was 1.1 kbp.

Fifty randomly chosen clones were sent for sequence analysis (Table 2). Introduced cDNA sequences were found in 28 of the clones with the remainder of the inserts the original cDNA cloning vector. Twenty of the identified cDNA sequences contained sequences where the majority of the translated sequence contained the 3 residue repeating sequence Gly-Xaa-Yaa which is characteristic of collagen and other triple-helix containing structures. The Gly is required every third residue as only this amino acid is small enough to fit within the centre of a triple-helix. The sequences containing the Gly-Xaa-Yaa repeat were grouped into 3 distinct classes and were termed Collagens A, B and C. The potential identity of other sequences was predicted from database comparisons.

An alignment of the collagen-like domains using the Expasy (ETH) program is provide as FIG. 1. For the 3 collagen segments, 126 residues in A and B and 120 in C chain. Of the non-Gly positions, 120-126 amino acids, 20 are common to all three chains. Between the A- and B-chains there are a further 21 positions in common (=41). Between the A- and C-chains there are a further 24 positions in common (=44). Between the B- and C-chains there are a further 13 positions in common (=33). There is also a tyrosine rich region at the C-terminus of the proteins, with each protein ending with a tyrosine.

TABLE 2

Identity of proteins contained within cDNA from *N. oligospilus* silk gland.

| Sequence type | Number of cDNA |
|---|---|
| Collagen A | 4 |
| Collagen B | 8 |
| Collagen C | 8 |
| Highly repetitive sequence | 3 |
| Peptidase | 1 |
| RNA helicase | 1 |
| Esterase | 1 |
| Actin | 1 |
| Translation elongation factor | 1 |

Example 2

Recombinant Expression of Sawfly Collagen-Like Silk Proteins

Three cDNA sequences, one from each of the three amino acid sequence types A (SF21), B (SF9) and C (SF30), were selected for expression studies. The cDNA were in pDONR 222. Restriction enzyme digestion sites were introduced into the original constructs by PCR mutagenesis using a Stratagene Site-directed Mutagenesis Kit (#200519) according to manufactures directions. The introduction of restriction enzyme digestion sites allowed isolation of the DNA for each sawfly silk gene and its insertion into an expression vector.

Sawfly collagen-like silk type A gene was inserted into pColdI vector via NdeI and EcoRI. Sawfly collagen-like silk type B gene was inserted pColdIV vector via NdeI and EcoRI. Sawfly collagen-like silk type C gene was inserted into pCold III via BamIII and SalI, and including a triple helix promoting sequence (V-domain) derived from the bacterial collagen Scl2 from *S. pyogenes*.

For expression of the sawfly silk protein, one colony of transformed *E. coli* BL21 cells was added to 100 ml starter culture medium, 2×YT-Amp and incubated at 37° C. with 200 rpm shaking overnight. This culture then had 100 ml fresh 2×YT-2% Glucose-Amp added, and was induced with 1 mM IPTG at 25° C. for 10 hour, then 20° C. for another 16 hours. The cell paste was harvested by centrifugation (3000×g for 30 min) The protein was associated with the cell pellet. For extraction, 1 gram of cell paste was resuspended in 10 ml of 40 mM Na/Phosphate buffer pH 8.0, and the cells burst by sonication. The cell lysate mixture was clarified by centrifugation (20 k×g for 40 min) and the clear supernatant retained.

Expressed silk proteins were purified used affinity purification using Pall 50 ml IMAC HyperCel column. Individual stock solutions of 200 mM Na/Phosphate, 4.4 M NaCl and 2 M imidazole were added to the clear lysate to final concentration of 20 mM Na/Phosphate buffer pH 7.6, 500 mM NaCl and 30 mM imidazole. This solution was loaded onto the affinity column, followed by washing the column with 5 column volumes of buffer A (20 mM Na/Phosphate buffer pH7.6, 300 mM NaCl and 40 mM Imidazole), sufficient for there to be no residual elution of material absorbing at 280 nm. The column was then eluted with a series of 1 column volume of buffer A, containing sequential stepwise increases of various amount of imidazole (70, 100, 150, 250 and 500 mM imidazole. Eluted fractions were monitored by absorption at 214 nm or 280 nm and were then analysed further by SDS-PAGE analysis. Samples containing the silk protein were then pooled and concentrated, and the buffer exchanged to 20 mM Phosphate pH 8.0, by membrane filtration (10 KDa cut off). This material was then further purified by ion-exchange chromatography on an anion-1ml Q column and Cation-1m SP column then further purify by Gel filtration on a Superdex 200 column. Many methods could be used to purify the protein.

Examples of sawfly silk protein expression from a pCold vector are shown in FIG. 2. In this example, SF30 was expressed as a fusion protein with a V-domain.

Example 3

Collagen-Like Silks Bind Fibroblasts

For cell adhesion studies, tissue culture 96 well microtiter plates were coated with 2 µg of proteins in PBS overnight at 4° C. After blocking with PBS containing 2% BSA for 2 h, mouse fibroblast L929 cells were seeded onto the coated surface at 250,000 cells $cm^{-2}$. Prior to seeding, cells were harvested by brief exposure to Tryple™Express (Gibco #12605) and resuspended in serum-free medium following by washing the cells with serum-free medium three times. Following 2 h exposure at 37° C./5% $CO_2$, the cells in the well were rinsed extensively with warm PBS twice, and apply 100 µl of MTS solution to the plates for further 1-3 hour incubation. Cells were also stained with phalloidin (for Actin) and DAPI (for DNA).

The collagen-like silk proteins of the invention support cell attachment of the L929 cells, presumably via the integrin receptor (FIG. 3). Silks of the invention were as good as mammalian collagen and fibronectin. These results show that the collagen-like silk proteins of the invention will be useful in the production of biomedical implants.

Example 4

Recombinant Sawfly Silk Proteins Form a Collagen-Like Structure

To demonstrate that sawfly collagen-like silk type A to C proteins are able to fold into triple-helical structures, the sequence of each type was expressed individually in *E. coli* (FIG. 4). The full length, expressed silk proteins were purified using affinity chromatography and gel permeation chromatography as follows: Cells were lysed by sonication in 40 mM sodium phosphate buffer, pH8.0, and the cell lysate clarified by centrifugation (20,000×g for 40 min) and the clear supernatant retained. The expressed silk proteins were purified by absorbing the clarified lysates on an IMAC HyperCel™ column (Pall), with elution by stepwise increments up to 500 mM imidazole, adjusted to pH 8 with HCl. Cross-flow filtration was used to lower the salt content and to concentrate the protein solution. Final purification was by gel permeation chromatography on a HiPrep Sephacryl™ S-200 column (GE Healthcare). The individual triple-helical collagen segments were prepared by digestion of the proteins with 0.1 mg/ml pepsin in 50 mM acetic acid. Purity of all products was assessed by SDS-PAGE.

Generally collagen is resistant to pepsin digestion and the treatment is commonly used to purify collagen molecules. Consistent with a collagen structure, a large proportion of the recombinantly produced sawfly silk proteins were resistant to pepsin digestion at 20° C. (FIG. 4A). In comparison, after denaturation of the proteins structure at high temperature, the entire molecule was protease sensitive. The circular dichroism spectra of the pepsin-resistant fragments confirmed the proteins were folded in the collagen triple-helix, with each spectrum showing positive ellipticity with maxima around 220 nm (Figure B).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/560,649 filed 16 Nov. 2011, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Antonicelli (2007) Curr. Top. Dev. Biol. 79:99-155.
Atkins (1967) J. Mol. Biol. 24:139-41.
Ayoub et al. (2007) PLoS One 13:e514.
Bini et al. (2004) J. Mol. Biol. 335:27-40.
Craig (2002) Comp. Biochem. Physiol. B Biochem. Mol. Biol. 133:493-507.
Craig and Riekel (2002) Comp Biochem. and Phys. Part B 133:247-255.
Dal Pra et al. (2005) Biomaterials 26:1987-99.
Elvin et al. (2010) Biomaterials 31:8323-8331.
Gosline et al. (1999) J. Exp. Biol. 202:3295-303.
Hayashi and Lewis (2000) Science 287:1477-9.
Hepburn and Kurstjens (1988) Apidologie 19:25-36.
Hepurn et al. (1979) Insect Biochem. 9:66.
Jin et al. (2002) Biomacromolecules 3:1233-9.
Kim et al. (2005) Biomaterials 26:2775-85.
Lucas and Rudall (1968) Extracecllular fibrous proteins: the silks. In Comprehensive Biochemistry eds. M Florkin, E H Stotz, Chapter 7. 26B:475-558. Amsterdam, London, New York: Elsevier.
Mathews (1975) Connective tissue: macromolecular structure and evolution. Springer-Verlag.
Nazarov et al. (2004) Biomacromolecules 5:718-26.
Needleman and Wunsch (1970) J. Mol. Biol. 48:443-453.
Persikov et al. (2005) J. Biol. Chem. 280:19343-19349.
Reiser et al. (1992) Nucleic Acids Research 32 (Web Server issue): W321-W326.
Ramshaw et al. (2000) J. Struct. Biol. 122:86-91.
Rudall (1962) In Comparative Biochemistry (ed: Florkin and Mason) 4:297-435 Academic Press, New York.
Rudall (1968) Comparative biology and biochemistry of collagen. In: Treatise on Collagen ed BS Gould Chapter 2 2A:83-137. London and New York: Academic.
Rudall and Kenchington (1971) Annual Review of Entomology 16:73-96.
Sutherland et al. (2006) Genome Res. 16:1414-1421.
Sutherland et al. (2010) Annu. Rev. Entomol. 55:171-88.
Tomita et al. (2011) Biotechnol. Lett. 33:645-654.
Vepari and Kaplan (2007) Prog. Polym. Sci. 32:991-1007.
Vollrath and Knight (2001) Nature 410: 541-8.
Zhang et al. (2012) PNAS 109:11981-11986.

The invention claimed is:

1. An expression vector comprising at least one polynucleotide which encodes a collagen-like silk polypeptide, wherein the polynucleotide comprises:
   i) a sequence of nucleotides as provided in any one of SEQ ID NOS: 7 to 12, 22 or 23;
   ii) a sequence of nucleotides encoding a polypeptide comprising an amino acid sequence as provided in any one of SEQ ID NOS: 1 to 6;
   iii) a sequence of nucleotides encoding a polypeptide comprising an amino acid sequence which is at least 60% identical to any one or more of SEQ ID NOS: 1 to 6;
   iv) a sequence of nucleotides encoding a biologically active fragment of ii) or iii), and/or
   v) a sequence of nucleotides which is at least 60% identical to any one or more of SEQ ID NOS: 7 to 12, 22 or 23, and wherein the polynucleotide is operably linked to a heterologous promoter.

2. A host cell comprising at least one exogenous polynucleotide which encodes a collagen-like silk polypeptide, wherein the polynucleotide comprises:
   i) a sequence of nucleotides as provided in any one of SEQ ID NOS: 7 to 12, 22 or 23;
   ii) a sequence of nucleotides encoding a polypeptide comprising an amino acid sequence as provided in any one of SEQ ID NOS: 1 to 6;
   iii) a sequence of nucleotides encoding a polypeptide comprising an amino acid sequence which is at least 60% identical to any one or more of SEQ ID NOS: 1 to 6;
   iv) a sequence of nucleotides encoding a biologically active fragment of ii) or iii), and/or
   v) a sequence of nucleotides which is at least 60% identical to any one or more of SEQ ID NOS: 7 to 12, 22 or 23.

3. The host cell of claim 2 which is a bacterial, yeast, animal or plant cell.

4. A substantially purified and/or recombinant collagen-like silk polypeptide which comprises:
   i) an amino acid sequence as provided in any one of SEQ ID NO's 1 to 6;
   ii) an amino acid sequence which is at least 60% identical to any one or more of SEQ ID NO's 1 to 6; and/or
   iii) a biologically active fragment of i) or ii);
   wherein the silk polypeptide is fused to at least one other polypeptide; or
   wherein the silk polypeptide is present in a silk fiber or copolymer and crosslinked to a surface of interest.

5. The polypeptide of claim 4 which is fused to at least one other polypeptide.

6. A transgenic organism comprising an exogenous polynucleotide which encodes a collagen-like silk polypeptide, wherein the polynucleotide comprises:
   i) a sequence of nucleotides as provided in any one of SEQ ID NOS: 7 to 12, 22 or 23;
   ii) a sequence of nucleotides encoding a polypeptide comprising an amino acid sequence as provided in any one of SEQ ID NOS: 1 to 6;
   iii) a sequence of nucleotides encoding a polypeptide comprising an amino acid sequence which is at least 60% identical to any one or more of SEQ ID NOS: 1 to 6;
   iv) a sequence of nucleotides encoding a biologically active fragment of ii) or iii), and/or
   v) a sequence of nucleotides which is at least 60% identical to any one or more of SEQ ID NOS: 7 to 12, 22 or 23.

7. A process for preparing a collagen-like silk polypeptide, the process comprising cultivating a host cell of claim 2 under conditions which allow expression of the polynucleotide encoding the polypeptide, and recovering the expressed polypeptide.

8. An isolated and/or recombinant antibody which specifically binds a polypeptide of claim 4.

9. A silk fiber, sponge, film, hydrogel or particle comprising at least one polypeptide of claim 4.

10. A copolymer comprising at least two polypeptides of claim 4.

11. A product comprising at least one polypeptide of claim 4, wherein the product is not produced by an insect.

12. A composition comprising at least one polypeptide of claim 4, and one or more acceptable carriers.

13. The composition of claim 12 which further comprises a drug and/or for use as a medicine, a medical device or a cosmetic.

14. A process for producing a product comprising collagen-like silk polypeptides, the process comprising;
   i) obtaining collagen-like silk polypeptides of claim 4, and
   ii) processing the polypeptides to produce the product.

15. A method of treating or preventing a disease, the method comprising administering a composition comprising at least one drug for treating or preventing the disease and a pharmaceutically acceptable carrier, wherein the pharmaceutically acceptable carrier is at least one polypeptide of claim 4.

16. A host cell comprising at least one expression vector of claim 1.

17. A process for preparing a collagen-like silk polypeptide, the process comprising cultivating a host cell of claim 16 under conditions which allow expression of the polynucleotide encoding the polypeptide, and recovering the expressed polypeptide.

18. The expression vector of claim 1, wherein the polynucleotide comprises a sequence of nucleotides encoding a polypeptide comprising an amino acid sequence which is at least 80% identical to any one or more of SEQ ID NOS: 1 to 6.

19. The expression vector of claim 1, wherein the polynucleotide comprises a sequence of nucleotides encoding a polypeptide comprising an amino acid sequence which is at least 90% identical to any one or more of SEQ ID NOS: 1 to 6.

20. The expression vector of claim 1, wherein the polynucleotide comprises a sequence of nucleotides encoding a polypeptide comprising an amino acid sequence which is at least 95% identical to any one or more of SEQ ID NO's 1 to 6.

21. The host cell of claim 2 which is a bacterial or yeast cell.

22. The polypeptide of claim 4 which does not have any hydroxyproline.

23. The polypeptide of claim 4 which comprises an amino acid sequence which is at least 80% identical to any one or more of SEQ ID NO's 1 to 6.

24. The polypeptide of claim 4 which comprises an amino acid sequence which is at least 90% identical to any one or more of SEQ ID NO's 1 to 6.

25. The polypeptide of claim 4 which comprises an amino acid sequence which is at least 95% identical to any one or more of SEQ ID NO's 1 to 6.

26. The polypeptide of claim 4 which is cross-linked to a surface.

27. The polypeptide of claim 4 which comprises at least 40 Gly-X-Y triplets where X and Y can be any amino acid.

28. The host cell of claim 16, wherein the collagen-like silk polypeptide which comprises at least 40 Gly-X-Y triplets where X and Y can be any amino acid.

* * * * *